United States Patent
DeShong et al.

(12)

(10) Patent No.: US 6,414,173 B1
(45) Date of Patent: Jul. 2, 2002

(54) HYPERVALENT SILANE AND SILOXANE DERIVATIVES AND THE USE THEREOF

(75) Inventors: Philip DeShong, Silver Spring; Molly E. Mowery, Elkridge; Eric D. Soli, Silver Spring; Amy S. Manoso, Baltimore; Michael C. Patterson, Odenton; Christopher J. Handy, Laurel, all of MD (US); Marc-Raleigh Brescia, Dayton, NJ (US)

(73) Assignee: University of Maryland, College Park, MD (US)

( * ) Notice: Subject to any disclaimer, the term of this patent is extended or adjusted under 35 U.S.C. 154(b) by 0 days.

(21) Appl. No.: 09/434,278

(22) Filed: Nov. 5, 1999

Related U.S. Application Data

(63) Continuation-in-part of application No. 09/346,705, filed on Jul. 2, 1999.
(60) Provisional application No. 60/091,487, filed on Jul. 2, 1999, provisional application No. 60/091,496, filed on Jul. 2, 1999, and provisional application No. 60/091,586, filed on Jul. 2, 1998.

(51) Int. Cl.$^7$ .................................................. C07F 7/08
(52) U.S. Cl. ........................ 556/11; 585/24; 536/18.7; 536/22.1
(58) Field of Search ............................ 556/11; 585/24; 536/18.7, 22.1

(56) References Cited

U.S. PATENT DOCUMENTS

| | | | | |
|---|---|---|---|---|
| 4,450,360 A | * | 5/1984 | Crivello et al. | 260/440 |
| 5,440,011 A | * | 8/1995 | Laine | 528/425 |
| 5,576,460 A | | 11/1996 | Buchwald et al. | 564/386 |
| 5,721,290 A | * | 2/1998 | Eckberg et al. | 522/315 |
| 5,747,172 A | * | 5/1998 | Crivello | 428/447 |
| 5,847,166 A | | 12/1998 | Buchwald et al. | 549/355 |
| 6,221,941 B1 | * | 4/2001 | Strauss et al. | 524/176 |

OTHER PUBLICATIONS

Brescia, M.-R., et al., "Regioselectivity in the Palladium–Catalyzed Addition of Carbon Nucleophiles to Dihydroopyran Derivatives," *J. Org. Chem.* 62:1257–1263 (Mar. 7, 1997).
Brescia, M.-R. and DeShong, O.,"Stereoselective Phenylation of Allylic Alcohol Derivatives by Palladium–Catalyzed Cross–Coupling with Hypervalent Silicon Complexes," *J. Org. Chem.* 63:3156–3157 (May 15,1998).
Denmark, S.E. and Wu, Z., "Synthesis of Unsymmetrical Biaryls from Arylsilacylcobutanes," *Org. Letters 1*: 1495–1498 (Sep. 30, 1999).
Denmark, S. E. and Choi, J. Y., "Highly Sterospecific Cross–Coupling Reactions of Alkenylsilacyclobutanes," *J. Am. Chem. Soc.* 121:5821–5822 (Jun. 6, 1999).
Denmark, S. E. and Wehril, D., "Highly Stereospecific, Palladium–Catalyzed Cross–Coupling of Alkenylsilanols," *Org. Lett.* 2:565–568 (2000).

Hatanaka, Y., et al., "A Convenient Synthesis of Substituted Heteroaromatic Compounds via the Palladium–Catalyzed Cross–Coupling Reaction of Organosilicon Compounds," *Heterocycles* 30:303–306 (1990).
Hatanaka, Y., et al., "Selective Synthesis of Unsymmetrical Biarlys via Palladium–Catalyzed Cross–Coupling of Arylfluorosilanes with Aryl Iodides," *Chem. Lett.* pp. 1711–1714 (1989).
Hatanaka, Y. and Hiyama, T., "Palladium–Catalyzed Carbonylative Coupling of Arylfluorosilanes with Aryl Iodides," *Chem. Lett.* pp. 2049–2052 (1989).
Hatanaka, Y. and Hiyama, T., "Highly Selective Cross–Coupling Reactions of Organosilicon Compounds Mediated by Fluoride Ion and a Palladium Catalyst," *SYNLETT* pp. 845–853 (1991).
Hatanaka, Y., et al., "Carbonylative Coupling Reaction of Organofluorosilanes with Organic Halides Promoted by Fluoride Ion and Palladium Catalyst," *Tetrahedron* 48:2113–2126 (1992).
Hatanaka, Y., et al., "Highly Selective Cross–Coupling Reactions of Aryl(halo)silanes with Aryl Halides: A General and Practical Route to Functionalized Biaryls," *Tetrahedron* 50:8301–8316 (1994).
Hirabayashi, K., et al., "A New Transformation Of Silanols. Palladium–Catalyzed Cross–Coupling with Organic Halides in the Presence of Silver (I) Oxide," *Org. Lett.* 1:299–301 (May 27, 1999).
Hiyama, T. and Hatanaka, Y., "Palladium–catalyzed cross–coupling reaction of organometalloids through activation with fluoride ion," *Pure & Appl. Chem.* 66:1471–1478 (1994).
Hiyama, T., In Metal–catalyzed Cross–coupling Reactions: Diederich, F., Stang, P. J., Eds.; Wiley–VCH Verlag GmbH: Weinheim, Germany, pp. 421–452 (Dec. 12, 1997).
Horn, K. A., "Regio– and Sterochemical Aspects of the Palladium–Catalyzed Reactions of Silanes," *Chem. Rev.* 95:1317–1350 (1995).
Inazu, T. and Kobayashi, K., "A New Simple Method for the Synthesis of N$^\alpha$–Fmoc–N$^\beta$–Glycosylated–L–Asparagine Derivatives," *SYNLETT* pp. 869–870 (1993).
Ito, M., et al., "A Simple and Convenient Synthesis of Alkyl Azides under Mild Conditions," *Synthesis* pp. 376–378 (1995).
Matsubara, K. and Mukaiyama, T., "High–Yielding Catalytic Synthesis of Glycosyl Azides from Peracylated Sugars," *Chem. Lett.* pp. 247–250 (1994).

(List continued on next page.)

*Primary Examiner*—Paul F. Shaver
(74) *Attorney, Agent, or Firm*—Sterne, Kessler, Goldstein & Fox P.L.L.C.

(57) ABSTRACT

Hypervalent silane and siloxane reagents (preformed or generated in situ) for transmetalation in palladium catalyzed reactions with derivatives of allylic alcohols, aryl halides, electron-withdrawing aryl bromides, and aryl triflates derived from phenols are disclosed. Also disclosed are methods of preparing glycosyl azides by reaction of an azide with a silyl ester in the presence of a phoshine.

25 Claims, No Drawings-

OTHER PUBLICATIONS

Maunier, V., et al., "A One–Pot Synthesis of Glycosyl Azides Using a Modified Staudinger Reaction," *J. Carbohydrate Chem.* 16:231–235 (Feb. 1997).

Mowery, M. E. and DeShong, P., "Cross–Coupling Reactions of Hypervalent Siloxane Derivatives: An Alternative to Stille and Suzuki Couplings," *J. Org. Chem.* 64:1684–1688 (Mar. 5, 1999).

Mowery, M. E. and DeShong, P., "Synthesis of Unsymmetrical Biaryls by Palladium–Catalyzed Cross Coupling Reactions of Arenes with Tetrabutlammonium Triphenyldifluorosilicate, a Hypervalent Silicon Reagent," *J. Org. Chem.* 64:3266–3270 (Apr. 9, 1999).

Mowery, M. E. and DeShong, P., "Improvements in Cross–Coupling Reactions of Hypervalent Siloxane Derivatives," *Org. Lett.* 1:2137–2140 (Dec. 7, 1999).

Nishihara, Y., et al., "Coupling Reactions of Alkynylsilanes Mediated by a Cu(I) Salt: Novel Syntheses of Conjugate Diynes and Disubstituted Ethynes," *J. Org. Chem.* 65:1780–1787 (2000).

Ogawa, T., et al., "Synthetic Studies on Nephritogenic Glycosides. Synthesis of N–(β–L–Aspartyl)–α–D–glucopyranosylamine," *Agric. Biol. Chem.* 47:281–285 (1983).

Prakash, G. K. S., et al., "Preparation of Secondary and Tertiary Cyclic and Polycyclic Hydrocarbon Azides," *J. Org. Chem.* 51:3215–3217 (1986).

Pilcher, A. S., et al., "Utilization of Tetrabutylammonium (Triphenysilyl)difluorosilicate as a Fluoride Source for Nucleophilic Fluorination," *J. Am. Chem. Soc.* 117:5166–5167 (1995).

Pilcher, A. S. and DeShong, P., "Utilization lof Tetrabutylammonium Triphenyldifluorosilicate as a Fluoride Source for Silicon–Carbon Bond Cleavage," *J. Org. Chem.* 61:6901–6905 (1996).

Sabesan, S. and Neira, S., "Synthesis of glycosyl phosphates and azides," *Carbohydrate Res.* 223:169–185 (1992).

Sengupta, S. and Sadhukhan, S. K., "Heck reaction of bis–arenediazonium salts with vinyltriethoxysilane: a new synthetic protocol for poly(1,4–arylenevinylene)s," *J. Chem. Soc. Perkin Trans.* 1:2235–2236 (Jul. 21, 1999).

Shibata, K., et al., "Preparation of functionalized biaryl compounds via cross–coupling reactions of aryltrialkoxysilanes with aryl bromides," *Chem. Commun.* pp. 1309–1310 (Jul. 21, 1997).

Soli, E. D.,et al., "Azide and Cyanide Displacements via Hypervalent Silicate Intermediates," *J. Org. Chem.* 64:3171–3177 (Apr. 9, 1999).

Soli, E. D. and DeShong, P., "Advances in Glycosyl Azide Preparation via Hypervalent Silicates," *J. Org. Chem.* 64:9724–9726 (Nov. 24, 1999).

Swamy, K. C. K. et al., "Pentacoordinate Acyclic and Cyclic Anionic Oxysilicates. A $^{29}$Si NMR and X–ray Structural Study," *J. Am. Chem. Soc.* 112:2341–2348 (1990).

Szarek, W. A., et al., "Photochemistry of Glycosyl Azides–II," *Tetrahedron* 34:4127–1433 (1978).

Takeda, T., et al., "The nephritogenic glycopeptide from rat glomerular basement membrane: synthesis of α–D–glucopyranosylamine derivatives," *Can. J. Chem.* 58:2600–2603 (1980).

Tropper, F. D., et al., "Phase Transfer Catalysis as a General and Stereoselective Entry into Glycosyl Azides from Glycosyl Halides," *Synthesis* pp. 618–620 (1991).

\* cited by examiner

HYPERVALENT SILANE AND SILOXANE DERIVATIVES AND THE USE THEREOF

CROSS REFERENCE TO RELATED APPLICATIONS

This application is a continuation-in-part of U.S. application Ser. No. 09/346,705, filed Jul. 2, 1999. This application also claims the benefit of provisional application Nos. 60/091,487, 60/091,496 and 60/091,586 filed Jul. 2, 1998. The contents of these applications are fully incorporated by reference herein.

BACKGROUND OF THE INVENTION

1. Field of the Invention

The invention is in the field of synthetic organic chemistry. In particular, the invention relates to hypervalent silane and siloxane reagents (preformed or generated in situ) for transmetalation in palladium catalyzed reactions with derivatives of allylic alcohols, aryl halides, and aryl triflates derived from phenols and the like. The hypervalent silicon species used in this invention may be a preformed hypervalent silicon species, e.g. TBAT (tetrabutylammonium triphenyldifluorosilicate) and tetrasubstituted siloxane derivatives which form hypervalent silicon species in situ when an anion (e.g. TBAF (tetrabutylammonium fluoride)) is added.

2. Related Art

Palladium-catalyzed cross-coupling reactions are versatile methods for the synthesis of carbon-carbon bonds in both a catalytic and stoichiometric manner. One of the more general methods developed in this class of reaction is the Stille coupling (and its myriad of variants) in which an organopalladium complex is allowed to react with a tin (IV) reagent to afford the coupling product (Scheme 1).

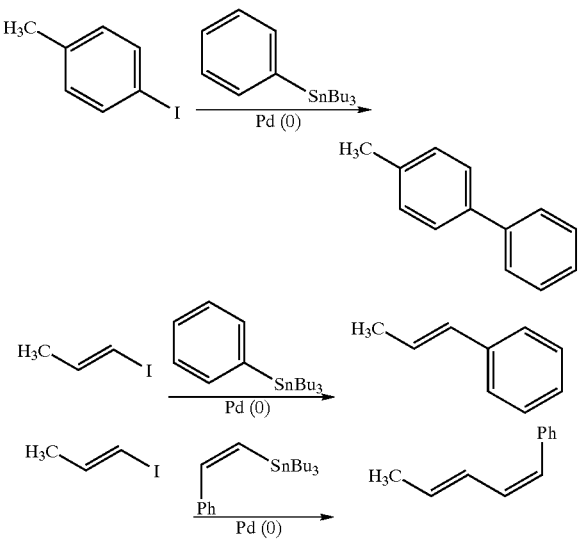

Scheme 1

(Trost, B. M., et al., "Organopalladium Compounds in Organic Synthesis and Catalysis," in *Comprehensive Organometallic Chemistry,* Vol. 8, Wilkinson, G., et al., eds., Pergamon, Oxford, England (1982), pp. 799–938; Tamao, K., "Coupling Reaction Between $sp^3$ and $sp^2$ Carbon Centers," in *Comprehensive Organic Synthesis,* Vol. 3, Trost, B. M., & Fleming, I., eds., Pergamon, Oxford, England (1991), pp. 435–480; Knight, D. W., "Coupling Reaction Between $sp^2$ Carbon Centers," in *Comprehensive Organic Synthesis,* Vol. 3, Trost, B. M. & Fleming, I., eds., Pergamon, Oxford, England (1991), pp. 481–578; Miyaura, N. & Suzuki, A., *Chem. Rev.* 95:2457–2483 (1995); Andersson, P. G., et al., *Tetrahedron* 50:559–572 (1994); Stille, J. K., *Angew. Chem.* 98:504–519 (1986) and references cited therein: Tsuji, T., *Palladium Reagents and Catalysis,* John Wiley & Sons, New York, N.Y. (1985); Stille, J. K., et al., *Org. Synth* 71:97–106 (1992) and references cited therein; Kalivretenos, A., et al., *J. Org. Chem.* 56:2883–2894(1991) and references cited therein; Gyorkos, A. C., et al., *J. Amer. Chem. Soc.* 112:8465–8472 (1990); Del Valle, L., et al., *J. Org. Chem.* 55:3019– 3023 (1990); Stille, J. K. & Sweet, M. P., *Tetrahedron Lett.* 30:3645–3648 (1989); Echavarren, A. M. & Stille, J. K., *J. Am. Chem. Soc.* 109:5478–5486 (1987); Stille, J. K. & Tanaka, M., *J. Am. Chem. Soc.* 109:3785–3786 (1987); Stille, J. K. & Groh, B. L., *J. Am. Chem. Soc.* 109:813–817 (1987); Stille, J. K., *Angew. Chem. Int. Ed. Engl.* 25:508–524 (1986); Scott, W. J. & Stille, J. K., *J. Am. Chem. Soc.* 108:3033–3040 (1986); Stille, J. K., *Pure Appl. Chem.* 57:1771–1780 (1985); Labadie, J. W. & Stille, J. K., *J. Am. Chem. Soc.* 105:6129–6137 (1983); Godschalx, J. & Stille, J. K., *Tetrahedron Lett.* 21:2599–2602 (1980); Milstein, D. & Stille, J. K., *J. Am. Chem. Soc.* 101:4992–4998 (1979); Milstein, D. & Stille, J. K., *J. Am. Chem. Soc.* 100:3636–3638 (1978); Farina, V., et al., *Org. React.* 50:1–652 (1997); Farina, V., *Pure Appl. Chem.* 68:73–78 (1996); Farina, V. & Roth, G. P., in *Advances in Metal-Organic Chemistry,* Vol. 5, Liebeskind, L. S., ed., J. A. I., Greenwich, England (1995); Trost, B. M., *Acc. Chem. Res.* 13:385–393 (1980); Trost, B. M., *Pure Appl. Chem.* 51:787–800 (1979); Trost, B. M., et al., *J. Am. Chem. Soc.* 100:3930–3931 (1978); Trost, B. M., *Tetrahedron* 33:2615–2649 (1977); *Pd-Catalyzed Alkylation of Allylic Substrates:* Class, Y. J. & DeShong, P., *Tetrahedron Lett* 36:7631–7634 (1995); Curran, D. P. & Suh, Y. -G., *Carbohydrate Res.* 171:161–191 (1987); Dunkerton, L. V. & Serino, A. J., *J. Org. Chem.* 47:2812–2814 (1982); Baer, H. H. & Hanna, Z. S., *Can. J. Chem.* 59:889–906 (1981); *Asymmetric Pd-Catalyzed Alkylations:* Trost, B. M. & Bunt, R. C., *Angew. Chem.* 108:70–73 (1996); Rieck, H. & Heimchen, G., *Angew Chem.* 107:2881–2883 (1995); von Matt, P. & Pfaltz, A., *Angew. Chem., Int. Ed. Engl.* 32:566–568 (1993); Other Reactions of Tin Reagents: Michell, T. N., *Synthesis* 803–815 (1992); Kosugi, M., et al., *Chem. Lett.* 1423–1424 (1997); Kosugi, M., et al., *Chem. Lett.* 301–302 (1997); Kosugi, M., et al., *J. Organomet. Chem.* 129:C-36-C-38 (1977)).

This is an exceedingly versatile process because it is highly tolerant of functional groups, provides a good yield of the coupled product, and retains the geometry of the alkene substrates. Accordingly, this process has been employed widely by the synthetic community for the formation of carbon-carbon bonds in pharmaceuticals and new materials. However, there are two serious limitations of this process for large scale synthesis: (1) the use of highly toxic tin (IV) substrates, and subsequently, (2) the removal of tin by-products.

Several remedies to these problems with Stille coupling have been developed, although no comprehensive solution has been developed to date. One of the more novel and potentially efficient solutions has been developed by Curran who has demonstrated that fluorous-based tin reagents can be utilized in Stille couplings (Hashimoto, J., et al., *J. Org. Chem.* 67:8341–8349 (1997)). Based upon previous studies by Zhu and Horvath, Curran has demonstrated that by employing fluorinated tin compounds as reagents, the unused tin reagent and the tin by-products of the Stille coupling protocol were removed by extraction with fluorocarbon solvents. This is a novel solution to the particularly vexing problem of removal of tin residues from the coupling product. In a research lab where small quantities of material are synthesized, handling of small quantities of tin reagents does not pose a significant health hazard (assuming it is performed in a hood). Also, it may be possible to remove the last vestiges of the toxic tin compounds from the desired product by chromatography, usually HPLC. (For a discussion of the purification of tin (IV) derivatives see: Hashimoto, J., et al., *J. Org. Chem.* 67:8341–8349 (1997); Crich, D. & Sun, S. R., *J. Org. Chem.* 61:7200–7201 (1996); Vedejs, E., et al., *J. Am. Chem. Soc.* 114:6556–6558 (1992).) However, in process/production labs that are responsible for multi-kilo synthesis, the handling of reagents, removal of tin by-products and excess reagent, and waste disposal of kilos of tin compounds poses a serious hazard to workers and a serious financial burden to the company. The situation is further complicated by the need to employ excess tin reagent in Stille couplings.

The solution is to replace toxic tin reagents by environmentally benign hypervalent silicon compounds. This solution would rectify both of the major concerns with the Stille coupling outlined above in that it would eliminate the inclusion of toxic tin reagents/by-products from the reaction protocol altogether. Another environmental consideration, as noted below, the silicate reactions could be performed in tetrahydrofuran (THF), a Class 3 solvent, rather than DMF.

Shibata, K. et al., *Chem. Commun.* 1309–1310 (1997), disclose cross coupling reactions of aryltrialkoxysilanes with aryl bromides. The reaction was carried out in the presence of TBAF, THF-DMF mixed solvent or toluene, and a palladium catalyst (palladium acetate or tetrakis(triphenylphosphine)-palladium(0).

SUMMARY OF THE INVENTION

The invention relates to a method for the preparation of a compound of Formula I:

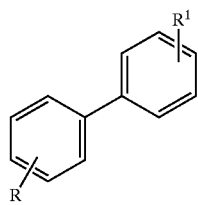

wherein R and $R^1$ are zero to three substituents, each of which is independently alkyl, alkenyl, aryl, alkanoyl, alkoxy or nitro comprising reacting a compound of Formula II:

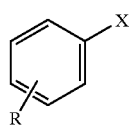

where R is defined above and X is Cl, Br, I or triflate (OTf) with a compound of Formula II:

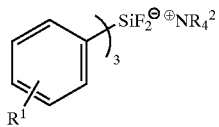

where $R^1$ is defined above and $R^2$ is an alkyl group, wherein the reaction is carried out in the presence of a Pd catalyst, under conditions whereby said compound of Formula I is produced.

The invention also relates to a method for the preparation of a compound having Formula IV:

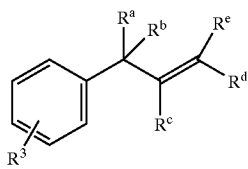

where $R^3$ is zero to three substituents, each of which is independently alkyl, alkenyl, aryl, alkanoyl, alkoxy or nitro, and $R^a$, $R^b$, $R^c$, $R^d$ and $R^e$ are independently hydrogen, optionally substituted alkyl, optionally substituted alkenyl, or $R^a$ and $R^e$ together form an optionally substituted carbocyclic or heterocyclic ring, comprising reacting a compound of Formula III:

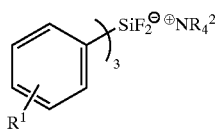

where $R^3$ is defined above and $R^2$ is an alkyl group, with a compound of Formula V:

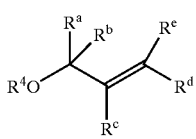

where $R^a$–$R^e$ are defined above and $R^4$ is an alky, aryl, aroyl or aralkyl group, wherein the reaction is carried out in the presence of a Pd catalyst, under conditions whereby said compound of Formula IV is produced.

The invention also relates to a method for the preparation of a compound having Formula IV:

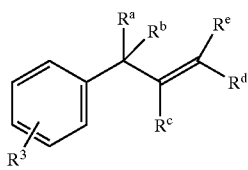

where $R^3$ is zero to three substituents, each of which is independently alkyl, alkenyl, aryl, alkanoyl, alkoxy or nitro, and $R^a$, $R^b$, $R^c$, $R^d$ and $R^e$ are independently hydrogen, optionally substituted alkyl, optionally substituted alkenyl, or $R^a$ and $R^e$ together form an optionally substituted carbocyclic or heterocyclic ring, comprising reacting a compound of Formula VI:

$$Y\ Si(OR^6)_3$$

wherein

Y is

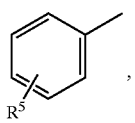

$R^5$ is zero to three substituents, each of which is independently alkyl, alkenyl, aryl, alkanoyl, alkoxy or nitro, and $R^6$ is alkyl or fluoroalkyl, with a source of fluoride ions or where the compound of Formula VII is added to the reaction as a preformed hypervalent fluoride; and a compound having Formula V:

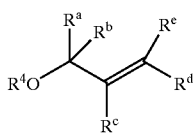

where $R^a$–$R^e$ are defined above and $R^4$ is an alkyl, aryl, aroyl or aralkyl group, wherein the reaction is carried out in the presence of a Pd catalyst, under conditions whereby said compound of Formula IV is produced.

In a preferred embodiment, the compound having Formula VII has the formula:

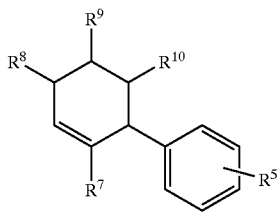

wherein $R^7$, $R^8$, $R^9$ and $R^{10}$ are independently hydrogen, alkyl or alkenyl.

In this embodiment, the compound of Formula V has the formula:

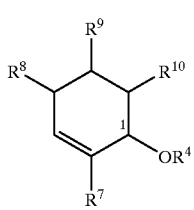

This coupling reaction occurs with inversion of configuration at carbon-1. Thus, the invention also relates to the preparation of a compound having Formula VIII

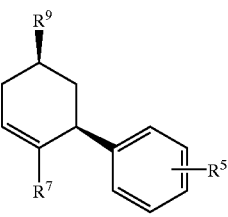

by the coupling of a compound having Formula IX

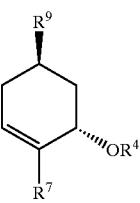

with a compound of Formula VI in the presence of a source of fluoride ions or where the compound of Formula VI is added as a preformed hypervalent fluoride.

Likewise, the invention also relates to the preparation of a compound having Formula X:

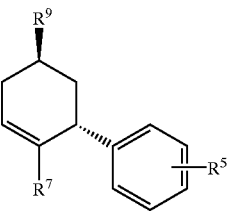

by the coupling of a compound having Formula XI

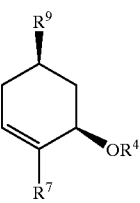

with a compound of Formula VI in the presence of a source of fluoride ions or where the compound of Formula VI is added as a preformed hypervalent fluoride.

The invention also relates to a method for the preparation of a compound of the Formula

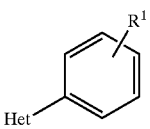

wherein Het is optionally substituted heteroaryl group and $R^1$ is zero to three substituents each of which is independently alkyl, alkenyl, aryl, alkanoyl, alkoxy or nitro, comprising reacting a compound for Formula:

Het—X wherein Het is defined above and X is Cl, Br, I or OTf, with a compound of Formula VI:

wherein
Y is

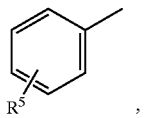

$R^5$ is zero to three substituents, each of which is independently alkyl, alkenyl, aryl, alkanoyl, alkoxy or nitro, and $R^6$ is alkyl, in the presence of a source of fluoride ions or where the compound of Formula VI is added as a preformed hypervalent fluoride; and a Pd catalyst, under conditions whereby said compound is produced.

The invention also relates to the Pd-catalyzed coupling of trivinyldifluorosilicon with aryl halides and triflates or compounds of Formula VI to give styrenes and alkyl vinyl derivatives.

The invention also relates to the preparation of a protected glycosylazide, comprising reacting a protected glycosyl, halide, triflate, trichloroimidate or tosylate with an azidotrialkylsilane in the presence of a source of fluoride ion or where instead a preformed hypervalent azidotrialkylsilicon fluoride is employed in place thereof, under conditions whereby the protected glycosylazide is produced.

The invention also relates to a method of preparing a compound having Formula XIII

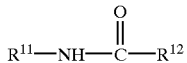

where $R^{11}$ is deoxyglycosyl, optionally substituted alkyl, optionally substituted aralkyl, optionally substituted heteroaralkyl or optionally substituted heterocycloalkyl and $R^{12}$ is alkyl or optionally substituted aralkyl, by reaction of a silyl ester of the Formula XIII:

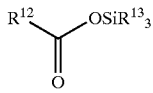

where each $R^{13}$ is independently an alkyl or aryl group, with $R^{11}$-$N_3$ in the presence of a trialkyl or triarylphosphine and a phenol, under conditions whereby the compound of Formula XII is produced.

This invention also relates to a method for preparing a compound of the formula:

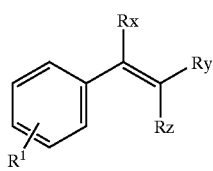

wherein $R^1$ is zero to three substituents, each of which is independently alkyl, alkenyl, aryl, alkanoyl, alkoxy or nitro, Rx, Ry and Rz are independently hydrogen, alkyl, alkenyl or Rx and Ry together form an optionally substituted carbocyclic or heterocyclic ring, comprising reacting a compound of Formula III

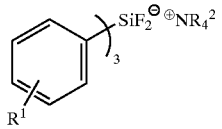

where $R^1$ is defined above and $R^2$ is an alkyl group, with a compound of Formula:

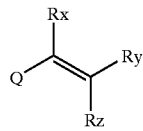

wherein Rx, Ry and Rz are defined above and Q is a halide or triflate, wherein the reaction is carried out in the presence of a palladium catalyst under conditions whereby said compound is produced.

Some illustrative reactions of the present invention are depicted in Scheme 2.

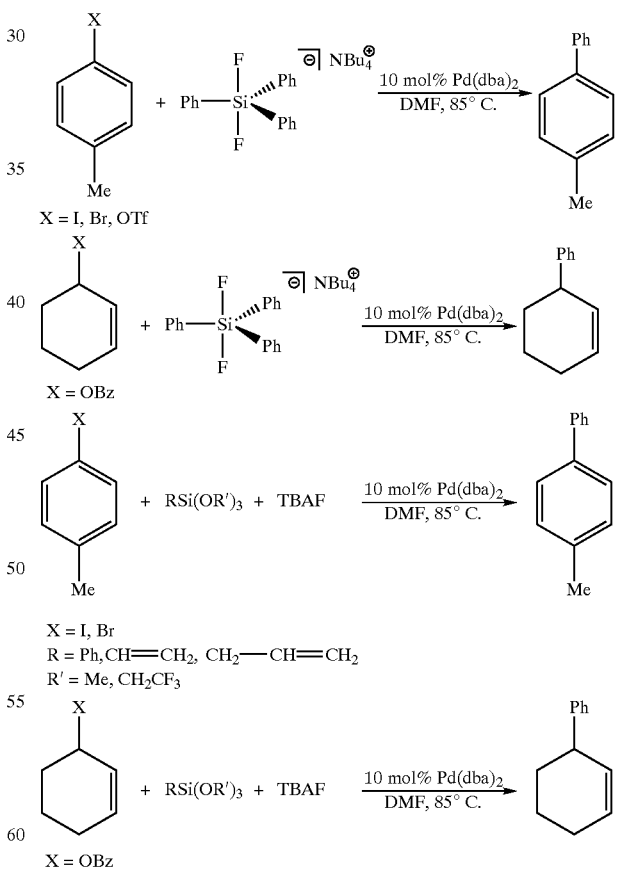

Scheme 2

DETAILED DESCRIPTION OF THE PREFERRED EMBODIMENTS

The invention relates to hypervalent silane and siloxane reagents (preformed or generated in situ) for transmetallation in palladium catalyzed reactions with derivatives of allylic alcohols, aryl halides (e.g. aryl iodides and electron-withdrawing aryl bromides), and aryl triflates. The hypervalent silicon species used in this invention are preformed hypervalent silicon species, e.g. tetraalkylrammonium tri-aryl and trialkyl heterofluorosilicates and siloxane derivatives which form hypervalent silicon species in situ when an anion (e.g. tetralkylammonium fluoride) is added.

Thus, in one aspect, the invention relates to a method for the preparation of a compound of Formula I:

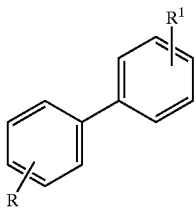

wherein R and $R^1$ are zero to three substituents, each of which is independently alkyl, alkenyl, aryl, alkanoyl, alkoxy or nitro comprising reacting a compound of Formula II:

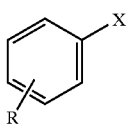

where R is defined above and X is Br, Cl, I or OTf with a compound of Formula III:

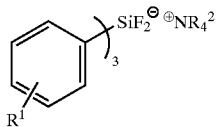

where $R^1$ is defined above and $R^2$ is an alkyl group, wherein the reaction is carried out in the presence of a Pd catalyst, under conditions whereby said compound of Formula I is produced.

Preliminary results of the Pd(0)-catalyzed cross-couplings with a compound of Formula III (e.g. tetrabutylammonium triphenyldifluorosilicate, (TBAT)) are summarized in Table 1. The general reaction studied is depicted in Scheme 3.

Scheme 3

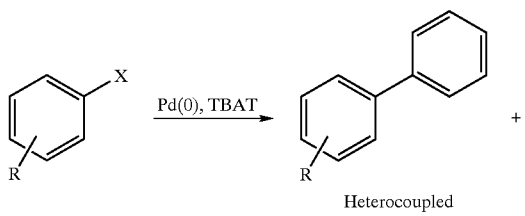

Heterocoupled

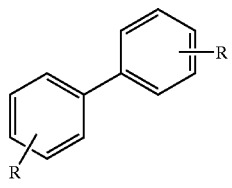

Homocoupled

It was found that the preformed hypervalent silicon compound, TBAT, transferred phenyl to various 2-, 3-, and 4- substituted aryl iodides. Optionally substituted aryl triflates derived from phenols and electron-poor aryl bromides were also suitable substrates for phenyl transfer. Results are summarized in Table 1. The reactions gave high yields, with most resulting in the 70–100% range, and very little of the homocoupled product was formed in most cases. It was found that the reactions tolerated changing the solvent from DMF to THF, although in most cases THF gave a slightly higher yield of the undesired, homocoupled product. Other solvents that may be used in the practice of the present invention include dioxane, toluene, acetonitrile and other like organic solvents.

It was found that changing the catalyst from allyl palladium chloride dimer to $Pd(dba)_2$ had virtually no effect on reaction outcome. Using TBAT is a high yielding, non-toxic and cost effective method for delivering a phenyl group to aryl iodides, electron-withdrawing bromides, and aryl triflates.

TBAT is distinctly advantageous for this application because it is a crystalline, non-basic substance that is freely soluble in organic solvents such as ether, toluene, THF, and dioxane. Accordingly, the fluoride displacement proceeds with a wide variety of substrates without base-catalyzed elimination (to form the alkene) occurring.

Derivatives of TBAT can be prepared and they too function as fluoride surrogates. By changing the electrondonating/withdrawing characteristics of the substituents attached to silicon, the relative nucleophilicity and basicity of the silicate anions can be modulated.

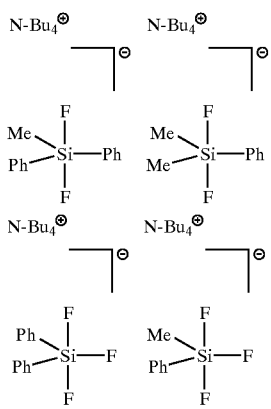

Other derivatives include compounds having the Formula:

wherein q is 1 or 2, r is 1 or 2 and s is 2 or 3.

TBAT (1) and the related derivatives of the present invention undergoes condensation with allylic alcohol derivatives such as 5 and 7 in the presence of Pd(0) catalysts to afford coupling products 6–9, respectively, in high yield (Scheme 4). This reaction is noteworthy because it occurs with complete inversion of configuration, in analogy with the tin-based Stille reaction. (For recent examples, see: Discodermolide: Smith, A. B., III, et al., *J. Am. Chem. Soc.* 117:12011–12012 (1995); Rapamycin: Nicolaou, K. C., et al., *J. Am. Chem. Soc.* 115:4419–4420 (1993).)

Scheme 4

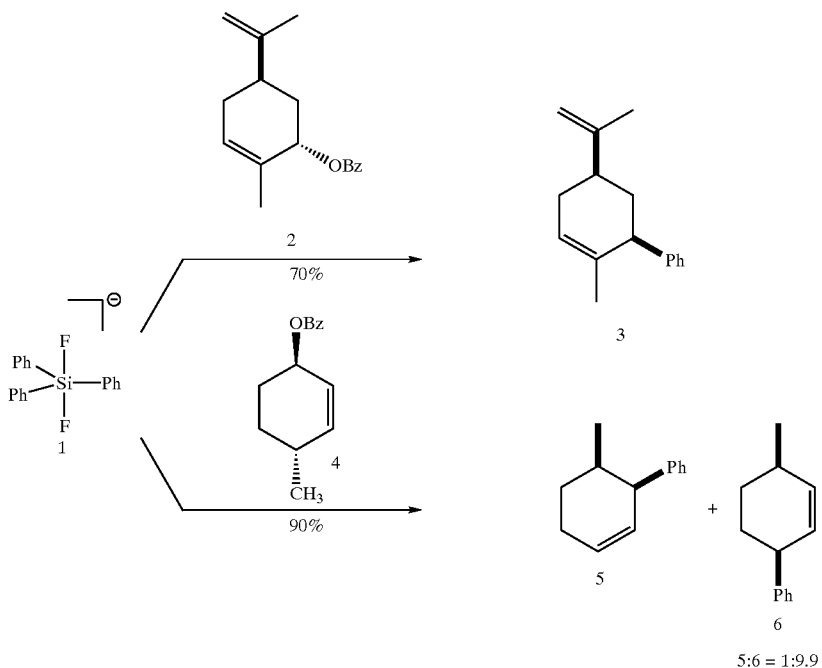

With allylic alcohol derivatives such as 2, 4, and 7, the coupling reaction with silicates occurred with complete stereoselectivity and modest regioselectivity in both carbocyclic and heterocyclic systems as shown by the examples in Schemes 4 and 5. The silicate coupling occurred in higher yield, under milder conditions, and with total stereoselectivity, whereas the coupling using the tin substrate resulted in modest loss of stereochemistry as summarized in Scheme 4. Unlike the tin reaction, it was observed that the presence of up to one equivalent of phosphine in the TBAT reaction media has no effect on either the yield or stereoselectivity of coupling. This is an important observation that allows for the preparation of chiral derivatives via the coupling protocol as discussed below.

Scheme 5

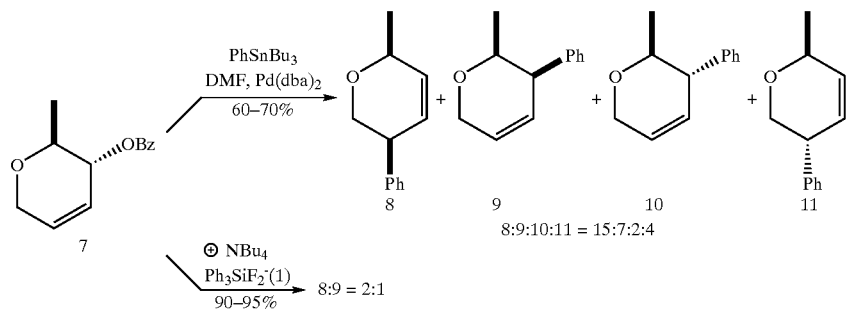

TBAT undergoes Pd(0)-catalyzed coupling with aryl iodides 12 to give unsymmetrical biaryls 13 in good to excellent yield (Scheme 6). Although the reaction conditions have not been optimized for TBAT, results indicate that both electron-donating and -withdrawing functionalities are tolerated on the aryl iodide. There are several noteworthy features of this process. First, the yields obtained to date are comparable to or exceed those obtained using tin substrates. Secondly, only traces of homocoupling product 14 are obtained, in contrast to the situation with tin reagents.

Scheme 6

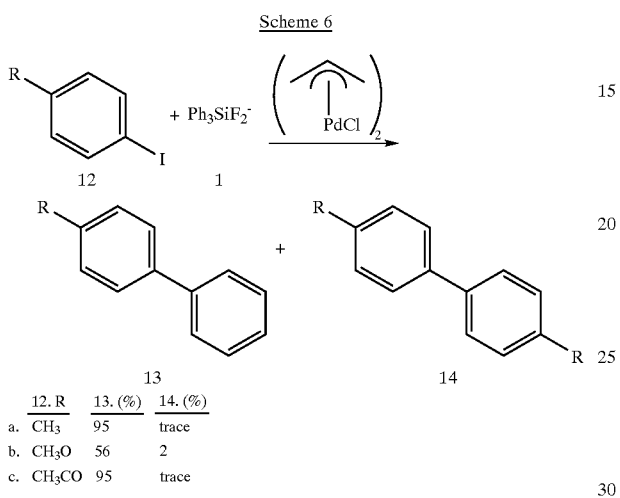

| 12. R | 13. (%) | 14. (%) |
|---|---|---|
| a. CH$_3$ | 95 | trace |
| b. CH$_3$O | 56 | 2 |
| c. CH$_3$CO | 95 | trace |

Hiyama and Hatanaka have reported that aryl silicon difluorides and trifluorides will couple with aryl iodides, and even bromides under certain circumstances, in the presence of Pd-catalysts to afford biaryls (Hiyama, T. & Hatanaka, Y., *Pure Appl. Chem.* 66:1471–1478 (1994); Hatanaka, Y., et al., *Tetrahedron* 50:8301–8316 (1994); Hatanaka, Y. & Hiyama, T., *Synlett.* 845–853 (1991); Hatanaka, Y., et al., *Tetrahedron* 48:2113–2126 (1992); Hatanaka, Y., et al., *Heterocycles* 30:303–306 (1990); Hatanaka, Y. & Hiyama, T., *Chem. Lett.* 2049–2052 (1989); Hatanaka, Y., et al., *Chem. Lett.* 1711–1714 (1989)). Generally, the yields of biaryl derivatives are excellent. The major limitation of the Hiyama/Hatanaka protocol is the requirement for the use of hydrolytically unstable, and strongly Lewis acidic silyl fluoride derivatives. The advantage of the silicate reagents of the present invention over the Hiyama/Hatanaka reagents is that silicates such as TBAT are stable, crystalline derivatives that are easily handled without precautions to avoid hydrolysis.

Thus, the invention also relates to a method for the preparation of a compound having Formula IV:

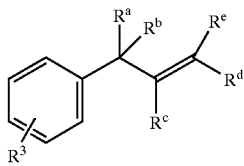

where R$^3$ is zero to three substituents, each of which is independently alkyl, alkenyl, aryl, alkanoyl, alkoxy or nitro, and R$^a$, R$^b$, R$^c$, R$^d$ and R$^e$ are independently hydrogen, alkyl, alkenyl, or R$^a$ and R$^e$ together form an optionally substituted carbocyclic or heterocyclic ring, comprising reacting a compound of Formula III:

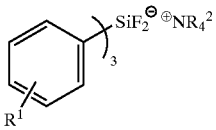

where R$^1$ is defined above and R$^2$ is an alkyl group, with a compound of Formula V:

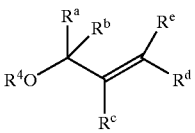

where R$^a$–R$^e$ are defined above and R$^4$ is an alkyl, aryl, aralkyl, alkanoyl, or aralkanoyl group,
wherein the reaction is carried out in the presence of a Pd catalyst, under conditions whereby said compound of Formula IV is produced.

The invention also relates to a method for the preparation of a compound having Formula IV:

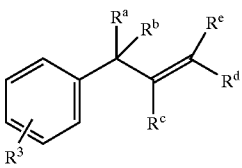

where R$^3$ is zero to three substituents, each of which is independently alkyl, alkenyl, aryl, alkanoyl, alkoxy or nitro, and R$^a$, R$^b$, R$^c$, R$^d$ and R$^e$ are independently hydrogen, alkyl, alkenyl, or R$^a$ and R$^e$ together form an optionally substituted carbocyclic or heterocyclic ring, comprising reacting a compound of Formula VI:

Y Si(OR$^6$)$_3$ wherein
Y is

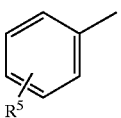

or an optionally substituted heteroaryl group,
R$^5$ is zero to three substituents, each of which is independently alkyl, alkenyl, aryl, alkanoyl, alkoxy or nitro, and R$^6$ is alkyl or fluoroalkyl, with a source of fluoride ions or where the compound having Formula VII is added to the reaction as a preformed hypervalent fluoride; and
a compound having Formula V:

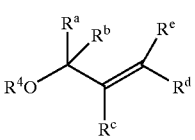

where R$^a$–R$^e$ are defined above and R$^4$ is an alkyl, aryl, aroyl, aralkyl, alkanoyl or aralkanoyl group, wherein the reaction is carried out in the presence of a Pd catalyst, under conditions whereby said compound of Formula IV is produced.

In a preferred embodiment, the compound having Formula VII has the formula:

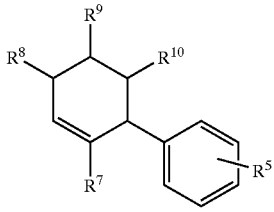

wherein $R^7$, $R^8$, $R^9$ and $R^{10}$ are independently hydrogen, optionally substituted alkyl or optionally substituted alkenyl.

In this embodiment, the compound of Formula V has the formula:

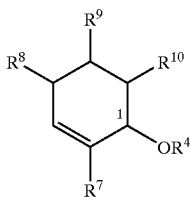

This coupling reaction occurs with inversion of configuration at carbon-1. Thus, the invention also relates to the preparation of a compound having Formula VIII

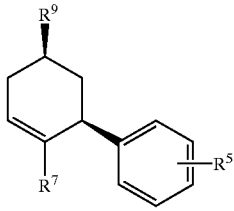

by the coupling of a compound having Formula IX

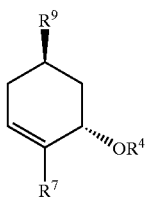

with a compound of Formula VI in the presence of a source of fluoride ions or where the compound of Formula VI is added to the reaction as part of a preformed hypervalent fluoride.

Likewise, the invention also relates to the preparation of a compound having Formula X:

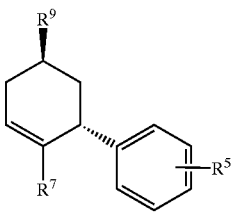

by the coupling of a compound having Formula XI

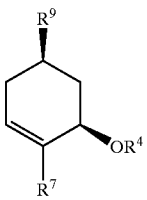

with a compound of Formula VI in the presence of a source of fluoride ions or wherein the compound of Formula VI is added to the reaction as part of a preformed hypervalent fluoride.

Some results of the Pd(0)-catalyzed cross couplings with siloxane derivatives are summarized in Table 2. Scheme 7 depicts the general reaction that was studied.

Scheme 7

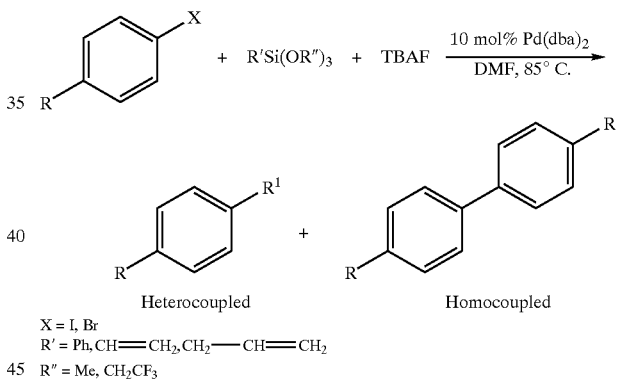

Heterocoupled    Homocoupled

X = I, Br
R' = Ph, CH=CH$_2$, CH$_2$—CH=CH$_2$
R" = Me, CH$_2$CF$_3$

The invention also relates to a hypervalent siloxane coupling reagent obtained by reacting a compound of Formula VI:

Y Si(OR$^6$)$_3$ wherein
  Y is an alkenyl group,

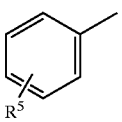

or an optionally substituted heteroaryl group,
$R^5$ is zero to three substituents, each of which is independently alkyl, alkenyl, aryl, alkanoyl, benzoyl, alkoxy or nitro, and $R^6$ is alkyl or fluoroalkyl, with a source of fluoride ions, e.g. tetraalkylammonium fluoride.

Phenyltrimethoxysilane, allyltrimethoxysilane, vinyltimethoxysilane, and phenyltris(trifluoroethoxy)silane transfer efficiently to 4'-iodotoluene giving yields of 80–90%, and reactions are complete within a few hours. Reaction conditions are amenable to changing the solvent from DMF to THF, although slightly more homocoupling is seen with THF. Changing the catalyst from Pd(dba)$_2$ to allyl palladium chloride dimer does not have an effect on the reaction outcome. The reaction seems to work well with the various aryl iodides, though yields are around 50–60% for the anisole and acetophenone aryl iodides. However, yields have been made higher (80–90%) through optimization of reaction conditions (see the examples). The coupling also occurred using the electron-deficient 4'-bromoacetophenone.

The reaction also works cleanly and quickly for transfer of phenyl to allylic benzoates, giving yields of 80–95% in about two hours time (Scheme 8 and Scheme 9).

Scheme 8

1.88 eq. PhSi(OMe)$_3$
3.82 eq. TBAF
10 mol% Pd(dba)$_2$
DMF, 85° C.
87%

2.18 eq. PhSi(OCH$_2$CF$_3$)$_3$
2.18 eq. TBAF
10 mol% Pd(dba)$_2$
DMF, 85° C.
95%

Scheme 9

2.0 eq. PhSi(OMe)$_3$
2.0 eq. TBAF
10 mol% Pd(dba)$_2$
DMF 85° C.
81%

The reactions may be carried out at a temperature of about room temperature to 130° C. Preferably, the reactions are carried out at about 85° C. when the solvent is DMF or about 75° C. when the solvent is THF.

For aryl triflates, the coupling does not yield the expected arylated product. Using electron-deficient or electron-rich triflates does not seem to influence the reaction. When phenyltrimethyoxysilane was used with the 1-napthyl, 4'-nitro, and 4'-carbomethoxy aryl triflates, only starting material was isolated. However, using phenyltris(trifluoroethoxy)silane surprisingly gave products derived from transfer of the trifluoroethoxy group (Scheme 10).

Scheme 10

2.18 eq. PhSi(OCH$_2$CF$_3$)$_3$
2.18 eq. TBAF
10 mol% Pd(dba)$_2$
DMF 85° C.
84%

Alternative forms of the invention include the synthesis of various substituted siloxane derivatives so that any type of aryl, allyl and vinyl group can be transferred. Varying the number of aryl groups on the siloxane so that multiple aryl transfers can occur to make the reaction very efficient is a useful application. It was found that with aryl triflates and PhSi(OCH$_2$CF$_3$)$_3$, the ethoxy anion ($^-$OCH$_2$CF$_3$) is transferred, giving an aryl substituted ether. Potential applications could include making siloxanes with various electron withdrawing groups on silicon so that when reacted with an appropriate triflate, different aryl substituted ethers can be made. Thus, the invention also relates to a method of preparing an optionally substituted alkoxyaryl compound, comprising reacting an optionally substituted aryl triflate with a phenyl trialkoxysilicate in the presence of a source of fluoride ions and a palladium catalyst under conditions in which the optionally substituted alkoxyaryl compound is produced.

In a preferred embodiment, the hypervalent silicon and siloxane reagents are preformed. The present invention provides for the use of cheap, non-toxic, chemically stable silicon and siloxane reagents to accomplish cross-coupling reactions in high yield. Current technology developed by Hiyama and coworkers starts with aryl(chloro)silanes and treating them with antimony trifluoride or copper fluoride makes the aryl(fluoro)silanes. The hypervalent silicon species is formed in situ by adding reagents such as TBAF or NaOH. This route is lengthy and uses expensive reagents. The reactions conditions are often limited in scope, such as only being able to use one type of palladium catalyst or one type of solvent. Our reaction conditions are amenable to other palladium catalysts and other solvents, while yields are not diminished, and times remain the same.

An alternative is the Stille reaction, which uses toxic tin reagents. The by-products of these reactions are extremely difficult to remove because they are water insoluble and non-volatile. Also, the reaction conditions are sometimes not tolerant of phosphines, which limits possibilities for making the reaction asymmetric. According to the present invention, the reaction tolerates an equimolar amount of phosphine to palladium catalyst. Thus, according to the present invention, it is possible to make the reaction asymmetric by adding a chiral phosphine ligand.

Extension of the silicate protocol to the synthesis of chiral aryl alkenes from achiral allylic alcohol derivatives is extremely important as there are no general means to accomplish this transformation in the repertoire of organic or organometallic synthesis. Trost has shown that allylic alcohol derivaties undergo a variety of transformations in a "chiral" manner upon exposure to Pd(0) catalysts incorporating chiral phosphine ligands and nucleophiles.(Trost, B.

M., *Accts. Chem. Res.* 29:357–364 (1996) and references cited therein; Trost, B. M. & Van Vranken, D. L., *Chem. Rev.* 96:395–422 (1996); Brost, B. M. & Radinov, R., *J. Am. Chem. Soc.* 119:5962–5963 (1997) and references cited therein). For example, as shown in Scheme 11, cyclohexyl acetate (15) underwent alkylation by malonate in the presence of Pd(0)-catalyst/phosphine 16 to afford malonate 17 in high yield and with almost complete enantioselectivity.

Since the silicate arylation tolerates the presence of phosphines, a chiral phosphine ligand may be employed in the arylation of allylic alcohol derivatives in an enantioselective manner. Examples of substrates are the benzoates 2 and 4 that undergo arylation by TBAT (1) in an achiral manner to provide alkenes 3 and 5/6, respectively (Scheme 11). There are a large number of chiral phosphine derivatives that can be employed, e.g. those developed by Trost for Pd-catalyzed alkylations (Trost, B. M., *Accts. Chem. Res.* 29:357–364 (1996) and references cited therein; Trost, B. M. & Van Vranken, D. L., *Chem. Rev.* 96:395–422 (1996); Brost, B. M. & Radinov, R., *J. Am. Chem. Soc.* 119:5962–5963 (1997) and references cited therein) and the chiral semicorrins of Pfaltz (Pfaltz, A., *Accts. Chem. Res.* 26:339–345 (1993); Pfaltz, A., *Acta Chem. Scand.* 50:189–194 (1996)). Other chiral ligands that can be used are taught by Saitoh, A., et al., *Tetrahedron-Asymmetry* 8:3567–3570 (1997); Morimoto, T., et al., *Synlett.* 7:783 (1997); Mino, T., et al., *Synlett* 5:583 (1997); Zhu, G. X., et al., *Tetrahedron Lett.* 37;4475–4478 (1996); Bolm, C., et al., *Tetrahedron Lett.* 37:3985–3988 (1996); Barbaro, P., *Organometallics* 15:1879–1888 (1996); Gamez, P., et al., *Tetrahedron-Asymmetry* 6:1109–1116 (1995); VonMatt, P., et al., *Helv. Chim. Acta* 78:265–284 (1995); and Kobota, H. & Koga, K., *Tetrahedron Lett.* 35:6689–6692 (1994).

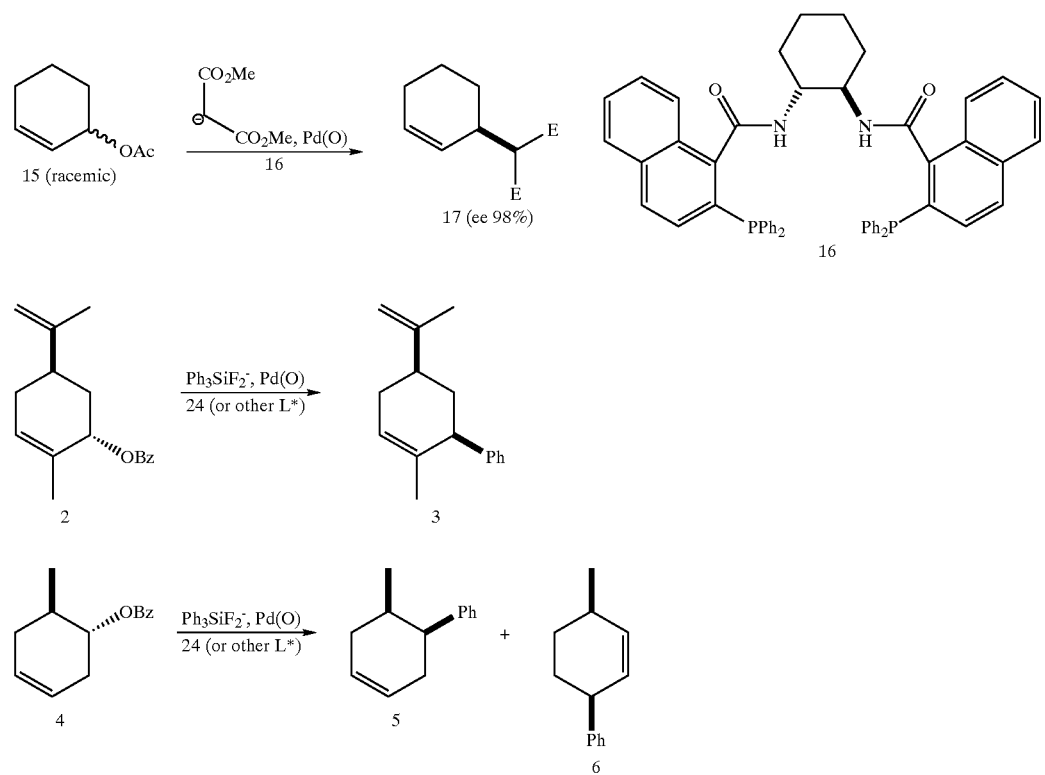

Scheme 11

The enantiomeric excess of the reaction mixtures (see Scheme 11) obtained with the various ligands may be determined using chiral HPLC analysis. Employing a chiral column available from Fred Khachik (Sumipax—OA 2000 (semichiral), 25 cm length, 4.6 mm internal diameter; 5 micron particle size), it was possible to obtain baseline separation of the enantiomers of alkene 3 (Scheme 11). Similar conditions will be applicable to separations of the enantiomers, of alkenes 5 and 6, respectively.

The Suzuki coupling couples aryl iodides and boronic acid derivatives under Pd(0) conditions. Often times, the boronic acid derivatives are difficult to prepare and purify, and are water soluble as well. Also, the reaction is limited to aryl iodides, which are expensive. In contrast, the reactions of the present invention are extremely versatile and have many potential applications including fine chemical synthesis, pharmaceutical synthesis, polymer synthesis, materials synthesis (including cross-linking reagents), and use in combinatorial libraries.

Other substrates that can be used in the practice of the invention include triacetylglucal (21) and allylic acetates 22 and 23 (Scheme 12). Glucal 21 is commercially available, while acetates 22 and 23 are available according to the methods of Byerley, A. L. J., et al., *Tetrahedron Lett.* 37:9093–9096 (1996); Larsen, E., et al., *Synthesis* 1037–1038 (1994)); and Crimmins, M. T. & King, B. W., *J. Org. Chem.* 61:4192–4193 (1996)), respectively. Arylation of substrates 21–23 with TBAT (1) is a model study for the synthesis of C-glycosyl derivatives. Recent reviews of C-glycoside syntheses: (Postema, M. H. D., *C-Glycoside Synthesis*, CRC Press, Boca Raton, Fla. (1995); Levy, D. E. & Tang, C., *The Chemistry of C-Glycosides*, Pergamon Press, New York, N.Y. (1995); Hanessian, S., *Total Synthesis of Natural Products: The "Chiron" Approach*, Pergamon Press, New York, N.Y. (1983); Qiao, I. & Vederas, J. C., *J. Org. Chem.* 58:3480–3482 (1993))

TABLE 2

| Entry | R | Catalyst | Solvent | TBAT (eq.) | Time (h) | Yield (%) Hetero | Homo |
|---|---|---|---|---|---|---|---|
| 1 | 4'-Ac | APC | DMF | 5 | 5 | 86 | 14 |
| 2 | 4'-Ac[a] | Pd(dba)$_2$ | DMF | 5 | 4.5 | 87 | 13 |
| 3 | 4'-Ac | APC | DMF | 2 | 2.1 | 100 | 0 |
| 4 | 4'-Ac[b] | APC | DMF | 2 | 25.5 | 90 | 0 |
| 5 | 4'-Ac | Pd(dba)$_2$ | DMF | 2 | 4.6 | 96 | 4 |
| 6 | 4'-Ac | APC | THF | 2 | 22 | 84 | 16 |
|  | 4'-Ac | APC | THF | 2 | 6 | 79 | 21 |
| 7 | 4'-Ac[c] | Pd(dba)$_2$ | THF | 2 | 19 | 76 | 24 |
| 8 | 4'-Ac | Pd(dba)$_2$ | dioxane | 2 | 6 | 83 | 17 |
| 9 | 4'-Ac[d] | Pd(dba)$_2$ | THF | 1 | 27.5 | 80 | 20 |
| 10 | 4'-Ac | APC | DMF | 1.2 | 23 | 93 | 0 |
| 11 | 4'-OMe | APC | DMF | 3 | 19 | 97 | 0 |
| 12 | 4'-OMe | Pd(dba)$_2$ | THF | 2 | 2.5 | 88 | 0 |
| 13 | 4'-Me | APC | DMF | 1.4 | 4 | 86 | 6 |
| 14 | 4'-Me | Pd(dba)$_2$ | THF | 2 | 25.5 | 64 | 24 |
| 15 | 3'-Me | APC | DMF | 1.4 | 24 | 97 | 3 |
| 16 | 3'-Me | Pd(dba)$_2$ | THF | 2 | 26.5 | 68 | 14 |
| 17 | 2'-Me | APC | DMF | 1.4 | 2 | 92 | 2 |
| 18 | 2'-Me | Pd(dba)$_2$ | THF | 2 | 5 | 87 | 10 |
| 19 | 4'-Ac | APC | DMF | 2 | 2.1 | 62 | 10 |
| 20 | 4'-Ac | Pd(dba)$_2$ | THF | 2 | 5 | 90 | 0 |
| 21 | 4'-Ac | APC | DMF | 2 | nr | 0 | 0 |
| 22 | 4'-OMe | APC | DMF | 2 | nr | 0 | 0 |
| 23 | 4'-OMe | APC | DMF | 2 | nr | 0 | 0 |
| 24 | 4'-Me | APC | DMF | 2 | nr | 0 | 0 |
| 25 | 4'-Me | APC | DMF | 2 | nr | 0 | 0 |
| 26 | 4'-Me | Pd(dba)$_2$ | THF | 2 | nr | 0 | 0 |
| 27 | 4'-NO$_2$ | Pd(dba)$_2$ | THF | 2 | 3.15 | 73 | 0 |
| 28 | 4'-Ac[e] | Pd(dba)$_2$ | THF | 2 | 18.5 | 73 | 0 |

APC = allyl palladium chloride
If DMF was used as a solvent, temp. was 95° C.; if THF was used as a solvent, temp. was 75° C.
[a]10 mol % Pd(dba)$_2$
[b]20 mol % PPh$_3$ added
[c]Trial 1 Recovered 0.010 g sm, 19 h, 66% het, 30% homo
[d]Recovered 0.034 g sm
[e]Recovered 0.004 g of sm

Scheme 12

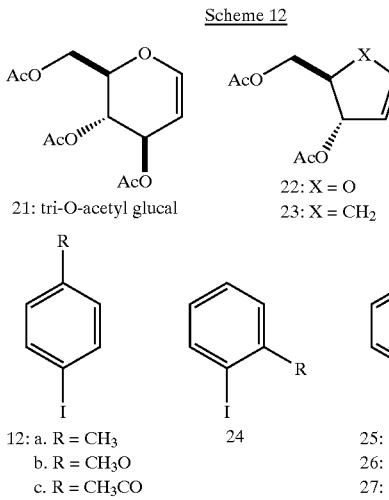

21: tri-O-acetyl glucal
22: X = O
23: X = CH₂

12: a. R = CH₃
   b. R = CH₃O
   c. R = CH₃CO

24

25: R = CH₃CO
26: R = NO₂
27: R = COOMe

Szabo (Szabo, K. J., *J. Am. Chem. Soc.* 118:7818–7826 (1996) and references cited therein), Barbaro, et. al. (Barbaro, P., et al., *Organometallics* 15:1879–1888 (1996)), and Oslob, et al. (Oslob, J. D., et al., *Organometallics* 16:3015–3021 (1996)) have investigated the effect of ligand coordination on the regioselectivity of pi-allyl Pd complexes when chiral phosphine complexes are employed in the allylic substitution reaction with stabilized nucleophiles. Their results demonstrate that distortion of the ligand coordination about the metal center has a strong influence on the regioselectivity of nucleophilic alkylation.

Examples of Pd catalysts that may be used in the practice of the invention include, without limitation, Pd(0) catalysts such as $Pd(dba)_2$, $Pd(PPh_3)_4$, $Pd_2(dba)_3$ and palladium salts such as allyl palladium chloride, palladium acetate, palladium chloride, and combinations of these palladium catalysts with trialkyl, triaryl phoshines, mixed aryl, alkylphoshines and chiral phosphines.

Aryl iodides are not ideal substrates for aryl couplings because of the difficulty of their preparation in comparison to the corresponding bromide or chloride analogs. According to the present invention, bromides and chlorides may be employed as substrates in the coupling. It has been proposed by Stille that bromides do not undergo coupling because Pd(0) catalysts are unable to undergo oxidative addition into the stronger carbon-bromine bond. (Stille, J. K., et al., *Org. Synth* 71:97–106 (1992) and references cited therein.) This limitation of the coupling can be circumvented with silicate reagents because it is possible to enhance the reactivity of the Pd-catalyst by addition of phosphines. Unlike the coupling with tin reagents where phosphine ligands sometimes inhibit coupling, it has been discovered that the silicate coupling protocol is not subject to inhibition by phosphine ligands. Accordingly, it is possible to enhance the ability of the Pd-catalyst to undergo oxidative addition into the carbon-bromine bond of aryl bromides by the addition of phosphines. A variety of aryl and alkyl phosphines with varying electron-donating and electron-withdrawing abilities may be employed.

Triflates 25–26 are ideal substrates for the coupling reaction because they are generally more available than their iodide counterparts. Triflates 25–26 are prepared from the respective phenol by standard methods. Stille has previously shown that aryl and vinyl triflates underwent coupling with tin derivatives in analogy to the iodide reaction. (Stille, J. K., et al., *Org. Synth* 71:97–106 (1992) and references cited therein) Hiyama too has utilized triflate derivatives in the coupling of phenyltrifluorosilanes. (Hiyama, T. & Hatanaka, Y., *Pure Appl. Chem.* 66:1471–1478 (1994); Hatanaka, Y., et al., *Tetrahedron* 50:8301–8316 (1994); Hatanaka, Y. & Hiyama, T., *Synlett.* 845–853 (1991)). Both Stille and Hiyama have noted that only aryl rings bearing a strongly electron-withdrawing group such as acetyl or nitro underwent the coupling under their conditions. It is possible to extend the silicate coupling reaction to aryl triflates, irrespective of the groups attached to the aromatic ring. One may add alkyl or aryl phosphines to the reaction mixture in an effort to modulate the activity of the Pd-catalyst.

Scheme 13

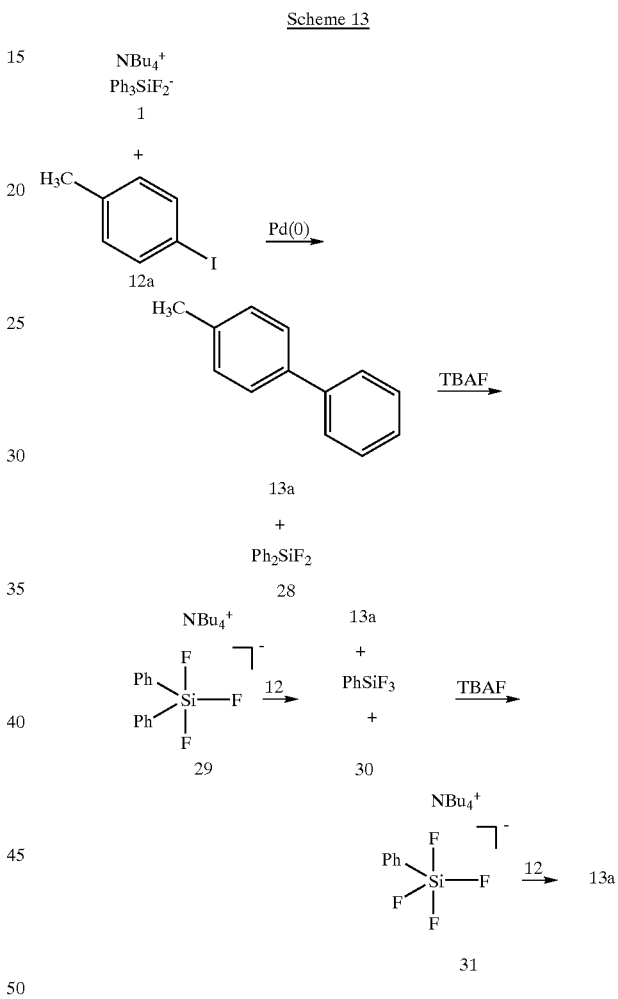

Multiple Aryl Transfers from TBAT. As outlined in Scheme 13, it is possible to induce multiple phenyl transfers from TBAT (1) by selecting the appropriate reaction conditions. Coupling of TBAT and aryl iodide 12 gives biaryl 13a. The by-product of the coupling is diphenylsilyldifluoride (28). If the reaction medium contains an equivalent of tetrabutylammonium fluoride (TBAF), then silyldifluoride 28 is converted into silicate 29 since the reaction of fluoride ion and related silicates is known to provide hypervalent silicate complexes. (The reaction of anisoylphenyldifluorosilane, methylphenyldifluorosilane and phenyltrifluorosilane with TBAF afforded the respective silicate homology of 29: Tamao, K., et al., *J. Organomet. Chem.* 506:85–92 (1996); Corriu, R. J. P. & Young, J. C., "Hypervalent Silicon Compounds," in *The Silicon-*

*Heteroatom Bond,* Patai, S & Rappaport, Z., eds., Wiley, New York, N.Y. (1991), Chapter 1, pp. 1–47; Tandura, S. N., et al., "Molecular and Electronic Structure of Penta- and Hexacoordinate Silicon Compounds," in *Topics in Current Chemistry,* Vol. 131, Boschke, F. L., ed., Springer-Verlag, New York, N.Y. (1986), pp. 99–186)). In analogy to the reactions of TBAT, silicate 29 undergoes crosscoupling with a second equivalent of iodide 12 to give biaryl 13a and phenyltrifluorosilane (30). Hiyama (Hiyama, T. & Hatanaka, Y., *Pure Appl. Chem.* 66:1471–1478 (1994)) has already shown that phenyltrifluorosilane and iodide 12 undergo coupling in the presence of TBAF and Pd-catalyst to produce biaryl 13a. Accordingly, under conditions in which the aryl iodide is unreactive towards TBAF, only 1.34 groups of TBAT are transferred.

Thus, the invention also relates to a method for the preparation of the compound having Formula I, wherein about one equivalent of the compound having Formula III is employed together with about three equivalents of a compound of Formula II. Of course, enough of a fluoride source must be added to ensure the production of the hypervalent silicates and the transfer of the three aryl groups.

Holmes has characterized 5-coordinate, anionic siloxane derivatives such as 36 and 37 (Scheme 14) in which the electronegative fluorines attached to silicon have been replaced by alkoxy groups. (Kumara Swamy, K. C., et al., *J. Am. Chem. Soc.* 112:2341–2348 (1990)). Siloxane complexes, i.e. 37, may be employed as alternatives to fluorosilicate derivatives such as TBAT (1). As outlined in Scheme 14, oxysilicate 37 is prepared by the standard protocol that has been employed for the synthesis of fluorosilicates (vide supra).

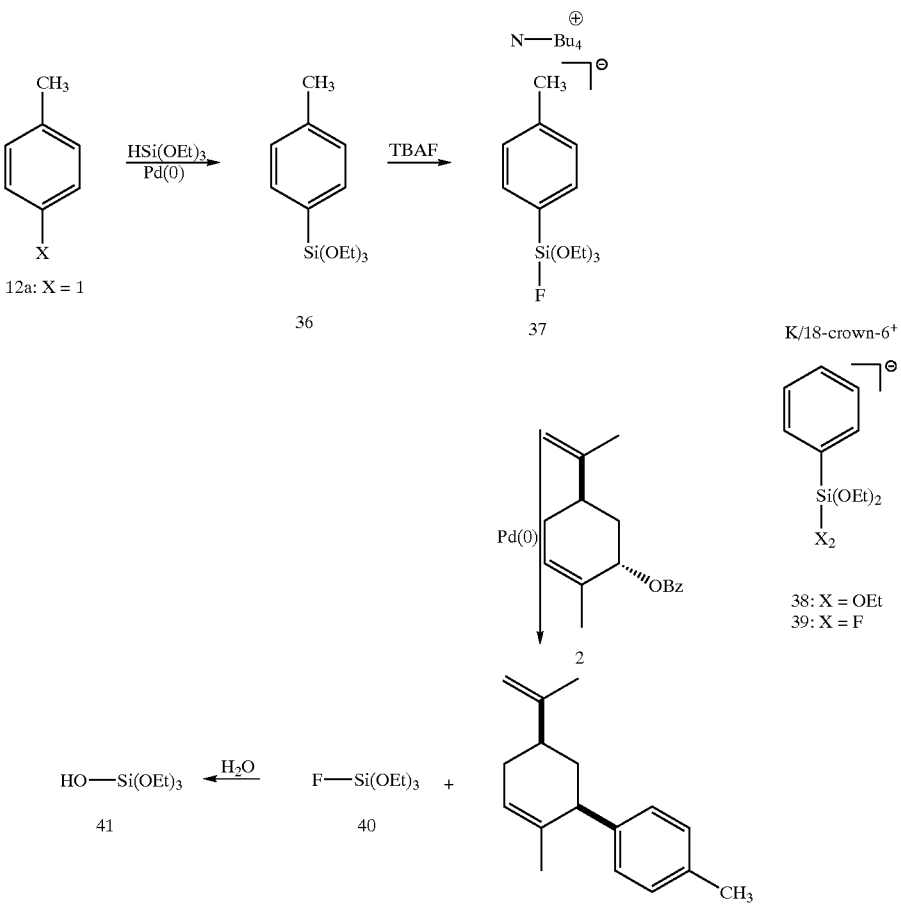

Scheme 14

Treatment of iodide 12a with triethoxysilane according to the procedure of Masuda (Murata, M., et al., *J. Org. Chem.* 62:8569–8571 (1997)) provides siloxane 36. Addition of TBAF to the siloxane results in formation of oxysilicate 37. (Kumara Swamy, K. C., et al., *J. Am. Chem. Soc.* 112:2341–2348 (1990)). This approach to the preparation of silicate derivatives has three particularly attractive features. First, it is possible to prepare structurally complex siloxane derivatives using the method of Masuda. A serious limitation of the fluorosilicate methodology as outlined above is that synthesis of the requisite silyl fluorides is not trivial. The use of stable siloxane derivatives such as 36 as precursors to the silicate reagents in the arylation protocol allows any aryl derivative of a silicate to be prepared from the corresponding phenol or iodide.

Second, in complex organic synthesis as applied in the pharmaceutical and fine chemical arenas, it is often necessary to carry the silyl derivative through several transformations prior to activation for coupling. In the case of the fluorosilanes, this would prove problematic. On the other hand, siloxanes are extremely stable to a wide variety of typical organic reagents, and they may easily be carried through complex organic sequences without undergoing degradation.

In summation, the ability to utilize siloxane derivatives for the generation of silicate reagents would be a significant advance in the silicon-based arylation methodology both from the chemical and environmental impact viewpoints.

A number of palladium catalysts were surveyed for the activation of aryl bromides, and it was found that a 1/2 ratio of Pd(OAc)$_2$/PPh$_3$ catalyst/ligand system was ideal for activating various aryl bromides (see Scheme 15 for examples). It was also found that o-tolylphosphine (P(o-tol)$_3$) is also a suitable ligand to use in place of triphenyl phosphine (PPh$_3$), although yields are slightly lower when this phosphine is used. The examples depicted below represent the three main "electronic" classifications of aryl bromides, all of which the Pd(OAc)$_2$/PPh$_3$ or Pd(OAc)$_2$/P(o-tol)$_3$ catalyst/ligand systems have been able to activate. These classifications include: electron-deficient (4-bromo-acetophenone), electron-neutral (4-bromo-toluene), and electron-rich (4-bromo-anisole).

Scheme 15

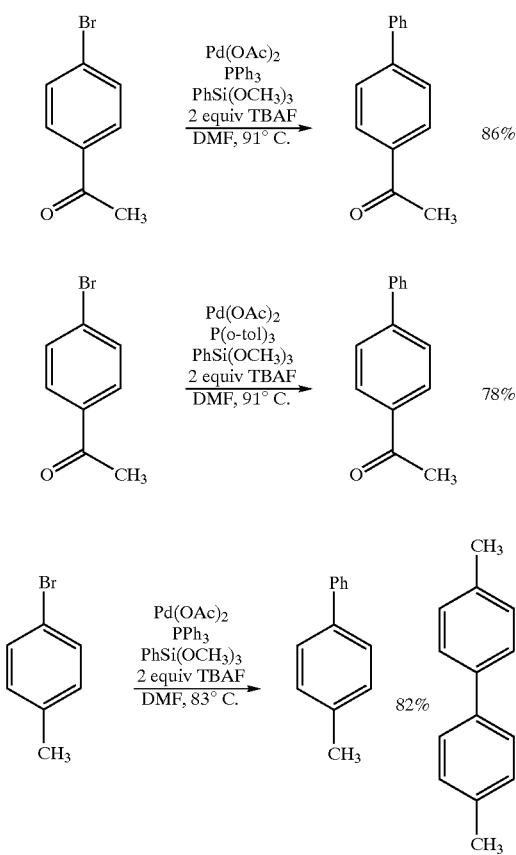

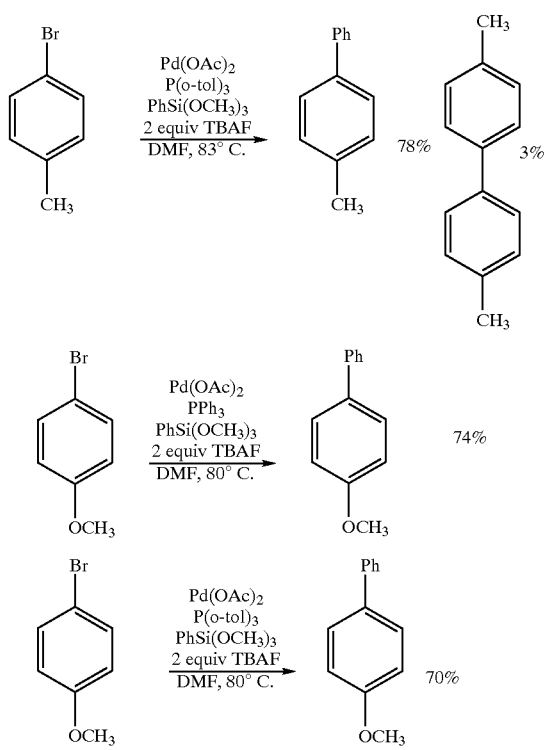

In addition, we have also been able to activate very hindered aryl bromides, such a 2-bromo-m-xylene (Scheme 16), although a much higher catalyst loading is required (at least 10 mol % Pd or higher).

Scheme 16

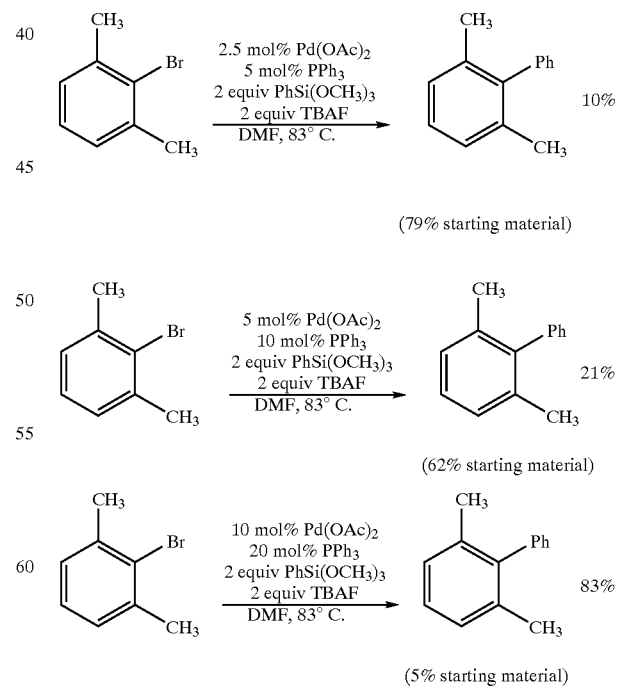

We have also performed extensive catalyst loading studies with the three main classifications of aryl bromides mentioned previously (Scheme 17). It was found that the minimum amount of catalyst required for these reactions is typically somewhere on the order of 2 to 3 mol % catalyst for substrates that are fairly unhindered.

Scheme 17

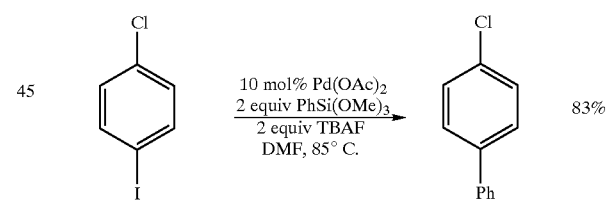

| | | | |
|---|---|---|---|
| 1 mol % Pd(OAc)$_2$ | 82% | 0% Hetero | 15% Hetero |
| 2 mol % PPh$_3$ | | 78% SM | 82% SM |
| 2.5 mol % Pd(OAc)$_2$ | 83% | 99% | 80% |
| 5 mol % PPh$_3$ | | | |
| 5 mol % Pd(OAc)$_2$ | 77% | 73% | 87% |
| 10 mol % PPh$_3$ | | | |
| 10 mol % Pd(OAc)$_2$ | 86% | 82% Hetero | 74% |
| 20 mol % PPh$_3$ | | 10% Homo | |

We have also been able to activate heterocycles such as 2- and 3-bromopyridines, as well 2- and 3-bromothiophenes (Scheme 18) in good yields. It was also found that changing the siloxane to phenyl tris(triethoxysiloxane) can significantly improve yields as well. Unfortunately the yields for the thiophene reactions are unavailable as the purification is still in progress, but $^1$H NMR analysis of the crude mixtures and comparison with published literature spectra does indeed indicate the cross-coupled products have been formed.

Scheme 18

Extension of the technology to aryl chlorides (Scheme 19) was not as successful. Using Pd(OAc)$_2$/PPh$_3$ seems to work for only electron deficient aryl chlorides (such as 4-chloro-acetophenone), and certainly not to completion. Extension to electron-neutral aryl chlorides (such as 4-chloro-toluene) fails completely (Scheme 19).

Scheme 19

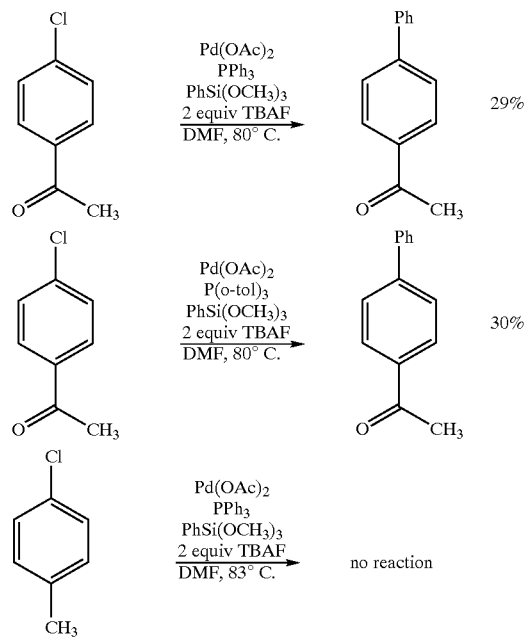

Lastly, we have been able to selectively activate an aryl-chloro-iodide in which only the iodide reacts (Scheme 20). Attempts to do the same for an aryl-bromo-iodide were not successful.

Scheme 20

The current focus continues to be on the activation of aryl chlorides, as well as investigating various substrates for the cross coupling reaction. We are also investigating different methodologies synthesize different aryl siloxanes so that there is the potential to transfer any aryl siloxane. Initial results with these cross couplings reactions have been extremely successful and we look forward to improving the technology so that its use becomes more commonplace.

Recently, the complex formed by treatment of azidotrimethylsilane with tetrabutylammonium fluoride, presumed to be hypervalent fluorotrimethylsilyl azide, was found to be an extremely reactive source of nucleophilic azide anion. (Ito, M. et al., *Synthesis* 376–378 (1995)). According to the present invention, the azido silicate may be used for the preparation of glycosyl azide derivatives.

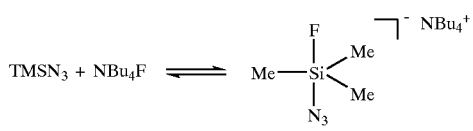

Reactions of azidotrimethylsilane with alkyl halides do not occur because of its low nucleophilicity compared with alkali metal azide salts. In 1986, Olah developed a procedure for the preparation of tertiary azides from tertiary halides using azidotrimethylsilane in the presence of a catalytic amount of tin(IV) chloride. (Prakash, G. K. S. et al., *J. Org. Chem.* 51:3215–3217 (1986)). This method, however, does not work well in the case of primary or secondary halides where a carbocation intermediate is not stable. On the other hand, we have found that secondary and primary halides, tosylates, trichloroimidates, and triflates are converted to the corresponding azides in high yields by the reaction with azidotrimethylsilane in the presence of fluoride anion under much milder conditions than are generally employed for the $S_N2$ reaction with alkali metal salts. Representative examples are summarized in Table 3.

Of particular concern was the ability to retain the protecting groups of the glycosyl derivatives during the displacement. Previous studies had demonstrated that azide displacements using the alkali metal salts resulted in removal of acetoxy groups under the strongly basic and nucleophilic reaction conditions. Acetoxy or benzyl ether protected sugars bearing an appropriate leaving group underwent efficient azide displacement with a slight excess of fluorotrimethylsilyl azide in THF at moderate temperatures to afford glycosyl azides in good to excellent yield. As noted in Table 3, the displacement occurred predominately with inversions of configuration and no deprotected or glycol elimination products were observed.

Initial studies probed the ability of azido complex to displace primary tosylates and secondary triflates of protected mannosyl derivatives (entries a and b; Table 3). In the first example, displacement of the primary tosylate of 42 proceeded readily at 65° C. to afford azide 43 in modest yield. Previous studies employing $NaN_3$ in DMF had given the azide in only 30–40% yield. At the more hindered secondary center, displacement occurred with equal facility. For example, mannosyl triflate 42 (1,3,4,6,-tetra-O-acetyl-2-O-trifluoromethanesulfonyl-β-D-mannopyranose; purchased from Aldrich Chemical Company and used without further purification) gave 2-azido-glucopyranose 43 in 73% yield. This reaction is noteworthy because the anomeric configuration was unaffected under these conditions. Alkali metal azide salts lead to deacetylation at the anomeric center in this and related systems resulting in anomerization. Other methods of azide introduction in the C-2 position include the following: azidonitration (Lemieux, R. U. et al., *Can. J. Chem.* 57:1244–1251 (1979)), azidophenylselenylation of glycols (Chelain, E. et al., *J. Carbohydr. Chem.* 15:571–579 (1996)), addition of halogenoazides to glycals (Bovin, N. V. et al., *Carbohydr. Res.* 98:25–35 (1981)), glucosamine treated with isoamyl nitrite (Dasgupta, F. et al., *J. Chem. Soc. Chem. Commun.* 1640–1641 (1989)), diazotransfer from glucosamine (Alper, P. et al., *Tetrahedron Lett.* 37:6029–6032 (1996); Vasella, A. et al., *Helv. Chim. Acta* 74:2073–2077 (1991)) and amine treatment with trifluoromethanesulfonyl azide (2,3,4,6-tetra-O-acetyl-α-D-glucopyranosylbromide; purchased from Acros Organics and recrystallized from diisopropyl ether prior to use). Compared to the above methods, the silicate-based azide displacement is superior in overall yield and ease of product isolation.

TABLE 2

Reaction of Silicate Anion with Glycosyl Acceptors.

| Entry | Substrate 42 | Product 43 | Temp. (° C.) | Time (h) | Yield[a] (%) |
|---|---|---|---|---|---|
| a | TsO-sugar(OAc)₃-OAc | N₃-sugar(OAc)₃-OAc | 65 | 6 | 77 |
| b | AcO-sugar-OTf-OAc | AcO-sugar-OAc-N₃ | 25 | 22 | 73 |
| c | AcO-sugar-Br | AcO-sugar-N₃ | 25 | 3 | 93 |
| d | AcO-sugar-Cl | AcO-sugar-N₃ | 65 | 29 | 85 |

TABLE 2-continued

Reaction of Silicate Anion with Glycosyl Acceptors.

| Entry | Substrate 42 | Product 43 | Temp. (°C.) | Time (h) | Yield[a] (%) |
|---|---|---|---|---|---|
| e | AcO-glucopyranosyl-Cl (tetra-OAc) | AcO-glucopyranosyl-N₃ (tetra-OAc) | 65 | 46 | 95[b] (α:β = 9:1) |
| f | AcO-glucopyranosyl-O-C(=NH)CCl₃ (tetra-OAc) | AcO-glucopyranosyl-OH (tetra-OAc) | 65 | 22 | 88 |
| g | BnO-glucopyranosyl-Cl (tetra-OBn) | BnO-glucopyranosyl-N₃ (tetra-OBn) | 65 | 5 | 92 |
| h | BnO-glucopyranosyl-O-C(=NH)CCl₃ (tetra-OBn) | BnO-glucopyranosyl-N₃ (tetra-OBn) | 65 | 48 | 48[c] (α:β = 1:1) |
| i | AcO-oxazoline sugar | AcO-glucopyranosyl-N₃, NHAc | 65 | 22 | 73 |
| j | AcO-glucopyranosyl-Cl, AcNH | AcO-glucopyranosyl-N₃, AcNH | 65 | 1.5 | 89 |

[a]Isolated material. All known compounds exhibited reported physical and spectroscopic properties.
[b]Isolated as a 9:1 (α/β) mixture of anomers.
[c]Isolated as a 1.1:1 (β/α) mixture of anomers.

In addition to primary and secondary azides 43a and 43b, β-anomeric azide 43c (43d), which serves as a precursor to glycopeptides, was prepared from known compounds. Treatment of commercially available α-bromide 42c (2,3,4,6-tetra-O-acetyl-α-D-glucopyranosylbromide was purchased from Acros Organics and recrystallized from diisopropyl ether prior to use) with silicate 1 afforded β-azide 43c in 93% yield. Similarly, α-chloride 42d underwent displacement to afford 43d. This facile method for preparation of 43d (42d) is less harsh and higher yielding than reported methods which include sodium azide displacement (Szarek, W. A. et al., *Tetrahedron* 34:1427–1433 (1978); Sabesan, S. and S. Neira, *Carbohydr. Res.* 223:169–185 (1992)), toxic solvents like hexamethylphosphoric triamide (Takeda, T. et al., *Can. J. Chem.* 58:2600–2603 (1980); Ogawa, T. et al.,*Agric. Biol. Chem.* 47:281–285 (1983)), phase transfer catalysis (Tropper, F. D. et al., *Synthesis* 618–619 (1992)) or toxic tin reagents (Matsubara, K. and T. Mukaiyama, *Chem. Lett.* 247–250 (1994)). Note that the reaction occurred by $S_N2$ displacement. β-Chloro anomer 42e was easily prepared and underwent displacement yielding azide 43e in 95% yield as a mixture of anomers (α:β=85:10). This conversion was not as stereoselective as those above and anomer separation was accomplished by column chromatography. An advantage to this silicate methodology is that the reactions can be performed in tetrahydrofuran which is easily removed while others require the use of toxic hexamethylphosphoric triamide.

Perbenzylated glycosyl donors, containing α-chloro and α-trichloroimidate substituents at the anomeric center, underwent azide displacement with hypervalent fluorotrimethylsilyl azide to afford glycosyl azides with a more robust protective group. As anticipated, α-chloroglucose 42g underwent stereospecific inversion of configuration to afford β-azide 43g (92%). Trichloroimidate 42h was also treated with the same conditions; however, it reacted sluggishly and afforded a 1.1:1 (β/α) anomeric mixture in 48% overall yield. Although the trichloroimidate was unsuccessful in the desired conversion, α-chloride 42g resulted in a direct synthesis of 43g as compared to other circuitous routes which include: a series of deprotection-protection sequences (Ogawa, T. et al., *Agric. Biol. Chem.* 47:281–285 (1983)), displacement of glucosylfluorides (Nicolaou, K. C. et al., *J. Chem. Soc., Chem. Commun.* 1155–1156 (1984)), use of tin (Fernandez-Resa, P. et al., *Eur. J. Med. Chem. Chim. Ther.* 21:245–249 (1986)), use of expensive in situ brominating agents (Saito, A. et al., *Tetrahedron Lett.* 38:3955–3958 (1997)) or non-commercially available nitrophenyl phosphorazidate (Mizuno, M. and Shiori, T., *J. Chem Soc. Chem. Commun.* 2165–2166 (1997)). The final glycosyl series investigated was the preparation of N-acetyl-glucosamine azide (entries i and j). Treatment of oxazoline 42i with silicate 1 afforded exclusively β-azide 43i in good yield. Alternatively, α-chloride 42j underwent azide displacement in 1.5 hours to give exclusively 43i. These results are comparable in yield and superior in ease of isolation of product. Some representative preparations of 43i involve the following: tin catalyst (Matsubara, K. and T. Mukaiyama, *Chem. Lett.* 247–250 (1994); Meinjohanns, E. et al., *J. Chem. Soc., Perkin Trans.* 1:405–415 (1995)), sodium or lithium azide (Paul, B. and W. Korytnyk, *Carbohyd. Res.* 67:457–468 (1978); Cowley, D. E. et al., *Carbohyd. Res.* 19:231–241 (1971); McDonald, F. E. and S. J. Danishefsky, *J. Org. Chem.* 57:7001–7002 (1992); Thiem, J. and T. Wiemann, *Angew. Chem. Int. Ed. Engl.* 29:80–82 (1990)), tetrabutylammomium azide (Auge, C. et al., *Carbohydr. Res.* 193:288–293 (1989)) and phase transfer conditions (Ogawa, T. et al., *Agric. Biol. Chem.* 47:281–285 (1983)).

Thus, the invention also relates to the preparation of a glycosylazide, comprising reacting a protected glycosyl tosylate, halide, triflate, trichloromidate or 1,2-oxazoline with an azidotrialkylsilane in the presence of a source of fluoride ion and a Pd catalyst under conditions whereby the glycosyl azide is formed.

Examples of glycosyl tosylates, halides, triflates, trichloroimidates and oxazolines include those in Table 3. Others include the 1-halo, 1-trichloroimidates, 1,2-oxazolines, and 5-tosylate, halide or triflate glucose, mannose, galactose, gulose, allose, altrose, talose, arabanose, and xylose Suitable protecting groups include alkanoyl (e.g. acetyl), and aralkyl (e.g. benzyl) groups.

It has been discovered that the reaction is catalytic in TBAF. The catalytic studies employed commercially available α-bromo glucose 42 that efficiently underwent azide displacement to provide azido glucose 43 (Scheme 21). In the first entry, 100 mol % (with respect to TMS-N$_3$) of TBAF was used and the expected β-azide 43c was formed in high yield. When the amount of TBAF was reduced to 50 mol %, the reaction still provided 43c in high yield; however, the reaction time was substantially longer at 20 hours. Finally, by reducing the amount of TBAF to 20 mol %, again, we obtained azide 43c in high yield; however, requiring 40 hours of stirring. There was no attempt to optimize the catalytic reactions by varying the reaction temperatures or solvent-types.

Scheme 21

| TBAF | Temp. (° C.) | Time (h) | Yield (%) |
| --- | --- | --- | --- |
| 100 mol % | 25 | 3 | 93 |
| 50 mol % | 25 | 20 | 91 |
| 20 mol % | 25 | 40 | 92 |

Thus, the invention also relates to the preparation of protected azidoglycosides with a catalytic amount of a fluoride ion source. A catalytic amount of a fluoride ion source is intended to mean that less than one equivalent of fluoride compared to trialkylsilylazide is employed in the reaction, preferably, less than about 0.5 equivalent, more preferably, less than about 0.2 equivalent.

Another interesting discovery was that the fluoride source is not exclusive to TBAF. It was possible to substitute tetrabutylammonium triphenyldifluorosilicate (TBAT, 1) as the source of nucleophilic fluoride. (Pilcher, A. S. et al., *J. Am. Chem. Soc.* 5166–5167 (1995); Pilcher, A. S. and P. DeShong, *J. Org. Chem.* 20:6901–6905 (1996).) TBAT is an excellent fluoride surrogate for TBAF because TBAT is crystalline, soluble in a wide range of organic solvents, nonbasic, and nonhygroscopic. When making the direct comparison of TBAF versus TBAT as the fluoride source, the reaction times, yields, and stereoselectivity were superior. For example, α-bromide 42c (Scheme 23) undergoes displacement with azidosilicate generated by either TBAF/TMS-N$_3$ or TBAT/TMS-N$_3$ in high yield and stereocontrol (Scheme 22). However, when TBAT is used as the fluoride source, the yield is slightly higher at 96% with a shorter reaction time of 90 min. There is one disadvantage to using TBAT as the fluoride source. The byproduct after fluoride delivery, triphenylsilyl fluoride, requires column chromatography in order to be removed from the reaction mixture. Additionally, although the reactions were catalytic in TBAF, we noticed that these transformations were not catalytic in TBAT.

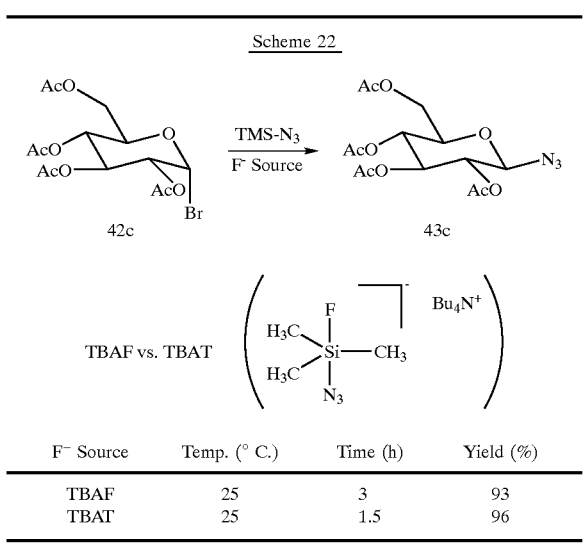

Scheme 22

| F⁻ Source | Temp. (° C.) | Time (h) | Yield (%) |
|---|---|---|---|
| TBAF | 25 | 3 | 93 |
| TBAT | 25 | 1.5 | 96 |

The usefulness of utilizing TBAT as the fluoride source was explored in some of the transformations which proved problematic (Scheme 23). As anticipated, α-chloride 42d underwent azide displacement with silicate generated by TBAF/TMS-$N_3$. The reaction requires longer stirring and elevated temperature to afford α-azide 43d in slightly lower yield than corresponding α-bromide 42c. When the fluoride source is changed from TBAF to TBAT, the conversion of 42d to the α-anomer of 43d is achieved in higher yield and requires a slightly shorter reaction time. Another transformation which proved difficult using the silicate generated by TBAF/TMS-$N_3$ was the conversion of β-chloride 42e to the a-anomer of 43e. When TBAF was employed as the fluoride source, the reaction afforded a 9:1 (α/β) anomeric mixture of 43e which could be separated by column chromatography. However, when TBAT was used as the fluoride source, not only did the overall yield increase, but the reaction also afforded only the desired α-anomer of 43e. The last entry is the conversion of converting α-trichloroimidate 43h to corresponding β-azide 43h. When TBAF was used, the reaction times were very long, anomeric selectivity was poor (resulting in a 1:1, α/β, mixture), and half of the starting material was hydrolyzed to the corresponding perbenzylated pyranose. By changing the fluoride source to TBAT, the reaction time was greatly reduced, the anomeric selectivity was improved (only the β-anomer of 43h was obtained), and the overall yield was improved. With the implementation of TBAT as the fluoride source, we were able to observe better overall reaction yields, better anomeric selectivity, and shorter reaction times.

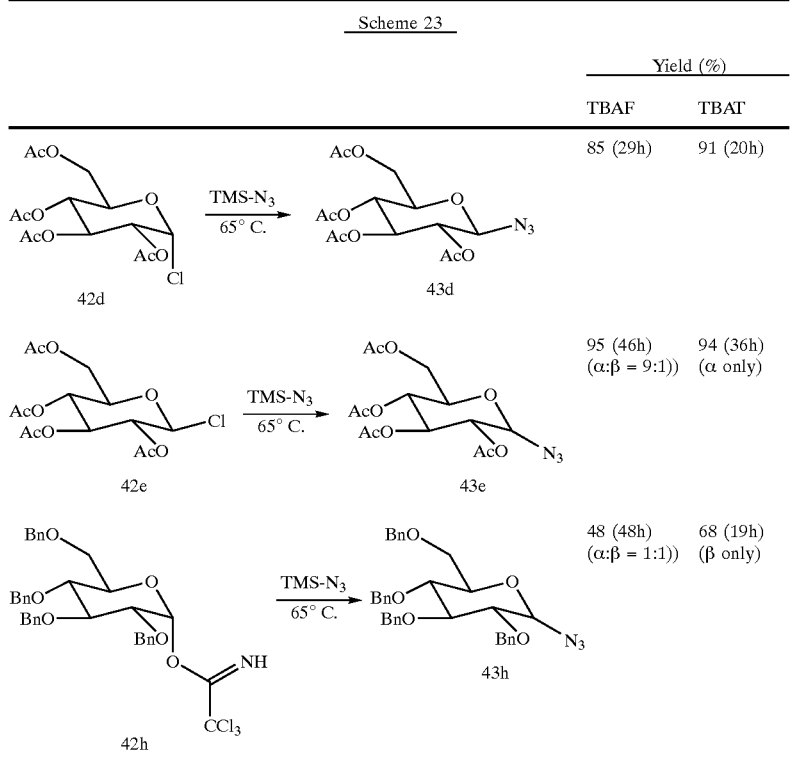

Phosphorus derivatives are often used to convert azides to amides by taking advantage of the Staudinger reaction (Staudinger, H. and J. Meyer, *Helv. Chem. Acta.* 2:619–635 (1919)). In this transformation, a phosphine or phosphite reacts with an azide to yield a phosphorimine (phosphazene) (Scheme 24). These nucleophilic phosphorus derivatives can be coupled with a carboxylic acid to give amide and phosphine oxide (Zaloom, J. et al., *J. Org. Chem.* 50:2601–2603 (1985); Homer, L. and A. Goss, *Liebigs Ann. Chem.* 591:117–134 (1955); Garcia, J. et al., *Tetrahedron Lett.* 25:4841–4844 (1984)).

Scheme 24

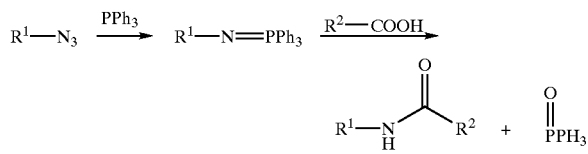

This sequence has several advantages over alternative technologies in the synthesis of glycosyl amide derivatives, especially with regard to the synthesis of the glycosyl asparagine moiety found in N-linked glycoproteins (Inazu, T and K. Kobayashi, *Synlett* 869–870 (1993)). Typical methods for synthesis of this linkage involve coupling of 1-glycosyl amines with various acid derivatives, acid chlorides (Maunier, V. et al., *J. Carbohydr. Chem.* 16:231–235 (1997)) or acids (Inazu, T and K. Kobayashi *Synlett* 869–870 (1993)). The major limitations of these approaches are (1) low yields of coupling product due to the hydrolytic lability of the amino substrates and (2) loss of configurational integrity at the anomeric center, again due to the lability of the amine. Application of the Staudinger reaction to the synthesis of amide derivatives avoids these limitations because a free amino derivative is not formed during the coupling process. Although the Staudinger reaction has been employed for the preparation of glycosyl amides (Inazu, T and K. Kobayashi, *Synlett* 869–870 (1993); Maunier, V. et al., *J. Carbohydr. Chem.* 16:231–235 (1997)), the reaction has not been studied in detail. Also, because we had an excellent method for constructing glycosyl azides that would serve as substrates in the coupling reaction, a detailed study of the Staudinger reaction was undertaken.

As shown in Table 4, Staudinger coupling of azides and carboxylic acids occurs in moderate to good yields using triphenyl- or tributylphosphine in toluene. Extensive experimentation with combinatons of solvents and phosphines has shown that the ideal solvents are toluene and dichloroethane and tributylphosphine is generally superior to triphenylphosphine. For example, entries a, b, and e indicate the potential of this methodology. Comparison of the yields of entries c and e demonstrates a limitation of this approach. In c, the yield of amide is reduced because the phosphorimine produced by treatment with phosphine reacts with the neighboring acetate ester. It has been shown that this is only a problem when the reaction with the ester is an intramolecular process. Attempts to induce intermolecular reaction between phosphorimines and esters is extremely slow. Note that when the acetate is replaced by a benzyl ether, the yield of product was increased dramatically (entry e).

TABLE 4

Staudinger reactions of various azides and glycosyl azides $R^1$—COOH + $R^2$—$N_3$ →(PPh₃ or PBu₃ / toluene)→ $R^1$C(O)N(H)$R^2$

| Entry | Carboxylic Acid | Azide | Phosphene | Product | Yield (%) |
|---|---|---|---|---|---|
| a | Ph–CO₂H | Ph–CH₂CH₂–N₃ | PPh₃ | Ph–C(O)–NH–CH₂CH₂–Ph | 69 |
| b | Ph–CO₂H | Ph–CH₂CH₂–N₃ | PBu₃ | Ph–C(O)–NH–CH₂CH₂–Ph | 70 |
| c | PhCO₂H | N₃-sugar(OAc)₃-O-OAc | PPh₃ | Ph–C(O)–NH-sugar(OAc)₃-O-OAc | 30 |
| d | Ph–CO₂H | AcO-sugar-N₃ (tetraacetyl glycosyl azide) | PBu₃ | AcO-sugar-NH-C(O)-CH₂-Ph | 21 |

TABLE 4-continued

Staudinger reactions of various azides and glycosyl azides

| Entry | Carboxylic Acid | Azide | Phosphene | Product | Yield (%) |
|---|---|---|---|---|---|
| e | 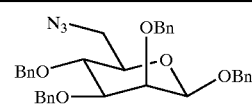 | 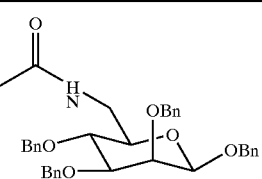 | PBu$_3$ |  | 65 |

A serious limitation of the classical Staudinger reaction for the synthesis of glycoprotein derivatives is that the reaction must be performed in toluene. Unfortunately, many sugar derivatives and most protein (or amino acid) derivatives that would serve as substrates are not soluble in non-polar solvents such as toluene and dichloroethane. In an effort to both improve the yields of coupling and to employ more polar substrates, a modified Staudinger procedure was developed. As summarized in Table 5, the acid is transformed into the silyl ester, thus rendering it freely soluble in non-polar solvents. However, with the silyl ester as substrate, condensation between the phosphorimine and ester does not occur. However, addition of p-nitrophenol (which protonates the phosphorimine and renders it more electrophilic) now results in rapid and efficient coupling. For example, using the modified Staudinger protocol coupling between phenylacetic ester and phenethyl azide occurred in virtually quantitative yield (entry a). Compare this result with the classical coupling reaction reported in entries a and b, Table 4.

Biotin is insoluble in toluene and is unreactive in the classical Staudinger coupling procedure; however, coupling of persilylated biotin and phenethyl azide gave a 45% yield of the amide derivative. This result clearly demonstrates the potential of this method for the preparation of amide derivatives of water soluble materials and glycoproteins by the Staudinger reaction.

Thus, the invention also relates to a method of preparing a compound having Formula XII $$R^{11}-NH-\underset{\underset{O}{\|}}{C}-R^{12}$$

where $R^{11}$ is deoxyglycosyl, optionally substituted alkyl, optionally substituted aralkyl, optionally substituted heteroaralkyl or optionally substituted heterocycloalkyl and $R^{12}$ is alkyl or optionally substituted aralkyl, by reaction of a silyl ester of the Formula XIII:

TABLE 5

Modified Staudinger coupling using silyl esters of carboxylic acids and p-nitrophenol.

| Entry | Silyl Ester | Product | Yield (%) |
|---|---|---|---|
| a | 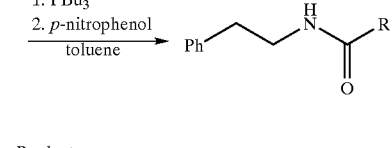 | 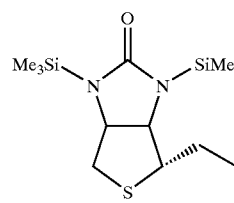 | 98 |
| b | 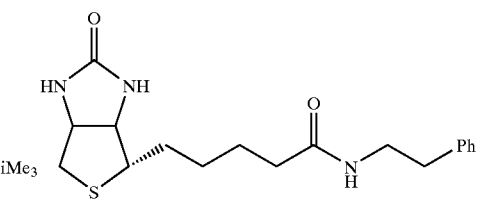 | | 45 |

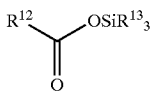

where each $R^{13}$ is independently an alkyl or aryl group, with $R^{11}$-$N_3$ in the presence of a trialkyl or triarylphosphine and a phenol, under conditions whereby the compound of Formula XII is formed. In a preferred embodiment, the reaction conditions include using a non-polar solvent such a toluene or dichloroethane.

Examples of $SiR^{13}_3$ groups include trimethylsilane, triethylsilane, and t-butyldimethylsilane.

Examples of phenols that can be used in the practice of the invention include p-nitrophenol, p-methoxyphenol and phenol.

Examples of trialkylphoshines include triethylphosphine, tributylphosphine, trimethylphosphine, tripentylphosphine and mixed aryl/alkyl phosphines (e.g. phenyl dimethylphosphine and diphenylmethylphosphine. Examples of triarylphosphines include triphenylphosphine.

With respect to the formulae, above:

Typical $C_{6-14}$ aryl groups include phenyl, naphthyl, phenanthryl, anthracyl, indenyl, azulenyl, biphenyl, biphenylenyl and fluorenyl groups.

Typical halo groups include fluorine, chlorine, bromine and iodine.

Typical $C_{1-6}$ alkyl groups include methyl, ethyl, propyl, isopropyl, butyl, sec-butyl, and tert-butyl groups. Also contemplated is a trimethylene group substituted on two adjoining positions on any benzene ring of the compounds of the invention.

Typical $C_{2-6}$ alkenyl groups include ethenyl, propenyl, isopropenyl, butenyl, and sec.-butenyl.

Typical arylalkyl groups include any of the above-mentioned $C_{1-6}$ alkyl groups substituted by any of the above-mentioned $C_{6-14}$ aryl groups.

Typical haloalkyl groups include $C_{1-6}$ alkyl groups substituted by one or more fluorine, chlorine, bromine or iodine atoms, e.g. fluoromethyl, difluoromethyl, trifluoromethyl, 1,1,1-trifluoroethyl, pentafluoroethyl, 1,1-difluoroethyl and trichloromethyl groups.

Typical alkoxy groups include oxygen substituted by one of the $C_{1-6}$ alkyl groups mentioned above.

Typical alkylthio groups include sulphur substituted by one of the $C_{1-4}$ alkyl groups mentioned above.

Typical alkanoyl groups include acetyl, propionoyl, butanoyl, pentanoyl, hexanoyl as well as aryl-substituted $C_{2-6}$ substituted alkanoyl groups.

Typical carbocyclic groups include $C_{3-8}$ rings which include optionally substituted cyclopropyl, cyclopentyl, cyclohexyl, cycloheptyl, cyclooctyl and the like.

Typical heterocyclic groups include tetrahydrofuranyl, pyranyl, piperidinyl, piperizinyl, pyrrolidinyl, imidazolindinyl, imidazolinyl, indolinyl, isoindolinyl, quinuclidinyl, morpholinyl, isochromanyl, chromanyl, pyrazolidinyl and pyrazolinyl groups.

Typical heteroaryl groups include any one of the following which may be optionally substituted with one or more alkyl, halo, or hydroxy groups: thienyl, benzo[b]thienyl, naphtho[2,3-b]thienyl, thianthrenyl, furyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, 5aH-carbozolyl, carbozolyl, β-carbolinyl, phenanthridinyl, acrindinyl, perimidinyl, phenanthrolinyl, phenazinyl, isothiazolyl, phenothiazinyl, isoxazolyl, furazanyl phenoxazinyl groups, 1,4-dihydroquinoxaline-2,3-dione, 7-amino isocoumarin, pyrido[1,2-a]pyrimidin-4-one, 1,2-benzoisoxazol-3-yl, 4-nitrobenzofurazan, benzimidazolyl, 2-oxindolyl and 2-oxobenzimidazolyl. Where the heteroaryl group contains a nitrogen atom in a ring, such nitrogen atom may be in the form of an N-oxide, e.g. a pyridyl N-oxide, pyrazinyl N-oxide, pyrimidinyl N-oxide and the like.

Typical amino groups include —$NH_2$, —$NHR^{14}$, and —$NR^{14}R^{15}$, wherein $R^{14}$ and $R^{15}$ are $C_{1-4}$ alkyl groups as defined above.

Optional substituents on the groups listed above include any one of the typical halo, haloalkyl, aryl, fused aryl, heterocyclic, heteroaryl, alkyl, alkoxy, alkenyl, arylalkyl, alkanoyl, and amino groups listed above as well as nitro, cyano, hydroxy, thiol, alkanoyloxy, azido, carboxy, carbonylamido, and alkylthiol.

Having now generally described the invention, the same will be more readily understood through reference to the following Examples which are provided by way of illustration, and are not intended to be limiting of the present invention, unless specified.

EXAMPLES

In all examples, all $^1H$ and $^{13}C$ NMR spectra were recorded on a 400 MHz spectrometer in $CDCl_3$ unless otherwise indicated. Coupling constants (J values are given in hertz (Hz)) and spin multiplicities are indicated by the following symbols; s (singlet), d (doublet), t (triplet), and m (multiplet). IR absorbances are reported in reciprocal centimeters ($cm^{-1}$). Gas chromatography was performed on a Hewlett-Packard 5890 GC equipped with a flame ionization detector using a 25 m capillary column coated with cross linked methyl silicone column. Tetrahydrofuran (THF) and dioxane were distilled from sodium/benzophenone ketyl. Pyridine and methylene chloride ($CH_2Cl_2$) were distilled from calcium hydride. Acetonitrile (MeCN) and dimethyl formamide (DMF) were distilled from molecular sieves. Methanol (MeOH) was dried and stored over molecular sieves. Glassware used in the reactions was dried overnight in an oven at 120° C. All reactions were performed under an atmosphere of nitrogen or argon unless noted otherwise.

Allyl palladium chloride dimer, allyl trimethoxysilane, phenyl trimethoxysilane, vinyl trimethoxysilane, benzoyl chloride (BzCl), (R)(−)-carvone, cerium chloride heptahydrate ($CeCl_3.7H_2O$), triflic anhydride, sodium borohydride ($NaBH_4$), all aryl iodides, all aryl bromides, all aryl chlorides and all arylphenols were purchased from Aldrich and used as received. Bis(disbenzylidene-acetone) palladium ($Pd(dba)_2$) was purchased from Acros Organics. Triphenylphosphine ($PPh_3$) was purchased from Aldrich and recrystallized from pentane prior to use. Tetrabutylammonium fluoride (TBAF) was used as a 1.0 M solution in THF and is commercially available from Acros Organics and Aldrich. Phenyl tris(trifluoroethoxy)silane was prepared according to the literature procedure. (Swamy, K. C. K. et al., J. Am. Chem. Soc. 112:2341–2348 (1990)). Tetrabutylammonium triphenyl difluorosilicate (TBAT) was prepared according to Pilcher, A. S. andDeShong, P., J. Am. Chem. Soc. 58:5130–5134 (1993) and is commercially available. 2,3,4,6-Tetra-O-acetyl-α-D-glucopyranosyl bromide was purchased from Acros Organics and recrystallized from diisopropyl ether prior to use. All compounds were determined to be >95% pure by GC and 1H NMR unless otherwise noted.

Example 1

Preparation of Phenyl Tris(trifluoroethoxy)silane

The siloxane was prepared according to the procedure of Swamy, K. C. K. et al.: bp 112–116.5° C./20 mmHg; IR (CCl$_4$) 3078 (m), 3057 (m), 2957 (s), 2896 (m), 1594 (s), 1574 (s), 1533 (s), 1151 (s), 867 (s), 808 (s); $^1$H NMR (CDCl$_3$) δ4.52 (q, J=8.1, 6H), 7.40–7.65 (m, 5H). The $^1$H NMR matched spectral data reported by Swamy, K. C. K. et al. $^{19}$F NMR and elemental analysis results are also reported by Swamy, K. C. K. et al.

Example 2

Preparation of 4-Methylbiphenyl—General Procedure

To a solution of 0.014 g (0.477 mmol) of 4-iodotoluene and 0.159 g (1.058 mmol) of phenyl trimethoxysilane in 10 mL of DMF was added 25 mg (0.043 mmol) of Pd(dba)$_2$. Then 1.10 mL (1.10 mmol) of TBAF was added to the reaction mixture via syringe. The reaction mixture was degassed to remove oxygen via one freeze-pump-thaw cycle. The brown reaction was heated at 95° C. for 2 h. The resulting brown mixture was quenched by the addition of 50 mL of water; the aqueous layer was then extracted with 4×50 mL Et$_2$O, and the combined organic layers were dried over MgSO$_4$ and concentrated in vacuo. Purification of the residue by flash chromatography (30 mm, 16 cm, pentane) gave 17 mg (40%) of 4,4'-dimethylbiphenyl. This matched an authentic sample (purchased from Aldrich) by GC and TLC.

Example 3

4-Methylbiphenyl

TLC R$_f$=0.47 (10% Et$_2$O/pentane); mp 44.5–46.5° C. (lit. mp 49° C. (EtOH); Rao, M. S. C. and Rao, G. S. K, *Synthesis* 231–239 (1987)); IR (CCl$_4$) 3081 (w), 3063 (w), 3038 (w), 2925 (w), 2863 (w), 1556 (s), 1531 (s); $^1$H NMR (CDCl$_3$) δ2.88 (s, 3H), 7.23 (m, 2H), 7.30 (t, J=7.6, 1H), 7.41 (t, J=7.6, 2H), 7.48 (d, J=8.1, 2H), 7.58 (d, J=7.3, 2H); $^{13}$C NMR (CDCl$_3$) δ21.1, 127.0, 128.7, 129.5, 137.0, 138.4, 141.2; LRMS (EI) 169 ((M+1), 19), 168 ((M$^+$), 100), 167 (63), 90 (21); HRMS (EI) calcd for C$_{13}$H$_{12}$ 168.0939 (M$^+$), found 168.0945. The IR and $^1$H NMR matched spectral data reported by Rao, M. S. C. and Rao, G. S. K.

Example 4

4-Acetylbiphenyl

TLC R$_f$=0.29 (10% EtOAc/hexane); mp 119.5–119.5° C. (lit. mp 119–120° C. (EtOH); Echavarren, A. M. et al., *J. Am. Chem. Soc.* 109:5478–6486 (1987)); IR (CCl$_4$) 3081 (w), 3038 (w), 3000 (w), 2931 (w), 2850 (w), 1691 (w), 1569 (s), 1538 (s); $^1$H NMR (CDCl$_3$) δ2.63 (s, 3H), 7.38 (t, J=7.3, 1H), 7.46 (t, J=7.4, 2H), 7.61 (d, J=7.2, 2H), 7.67 (A of AB quartet, J$_{AB}$=8.4, 2H), 8.02 (B of AB quartet, J$_{AB}$=8.4, 2H); $^{13}$C NMR (CDCl$_3$) δ26.6, 127.2, 128.9, 135.9, 139.0, 145.6, 197.7; LRMS (EI) 197 ((M+1), 10), 196 ((M$^+$), 59), 181 (100), 153 (35); HRMS (EI) calculated for C$_{14}$H$_{12}$O 196.0888 (M$^+$), found 196.0883. The IR and $^1$H NMR matched spectral data reported by Echavarren, A. M. et al.

Example 5

4-Methoxybiphenyl

TLC R$_f$=0.46 (10% EtOAc/hexane); mp 83.5–85.5° C. (lit. mp 90° C. (EtOH); Neeman, M. et al., *Tetrahedron* 6:36–47 (1959)); IR (CCl$_4$) 3081 (w), 3047 (w), 3006 (w), 2391 (w), 2856 (w), 2838 (w), 1563 (s), 1512 (s), 1250 (s), 1006 (m); $^1$H NMR (CDCl$_3$) δ3.38 (s, 3H), 6.95–6.97 (m, 2H), 7.40 (t, J=7.7, 2H), 7.50–7.54 (m, 5H), $^{13}$C NMR (CDCl$_3$) δ55.4, 114.2, 126.6, 126.7, 128.2, 128.7, 135.2; LRMS (EI) 185 ((M+1), 15), 184 ((M$^+$), 100), 169 (39); HRMS (EI) calculated for C$_{13}$H$_{12}$O 184.0888 (M$^+$), found 184.0885. The IR and $^1$H NMR matched spectral reported by Neeman, M. et al.

Example 6

4-Chlorobiphenyl

TLC R$_f$=0.56 (pentane); mp 77–77° C. (lit. mp 77–77.5° C. (MeOH/H$_2$O); Chikasawa, K. and Uyeta, M., *Chem. Phann. Bull.* 28:57–61 (1980)); IR (CCl$_4$) 3112 (w), 3089 (w), 3032 (w), 1584 (s), 1526 (s), 1479 (s), 836 (s); $^1$H NMR (CDCl$_3$) δ7.33–7.56 (m, 9H); $^{13}$C NMR (CDCl$_3$) δ127.0, 127.6, 128.4, 128.9, 139.7,140.0; LRMS (EI) 190 ((M+2), 32), 189 ((M+1), 13), 188 ((M$^+$), 100); 152 (28); HRMS (EI) calculated for C$_{12}$H$_9$Cl 188.0398 (M$^+$), found 188.0386. The IR and LRMS matched spectral data reported by Chikasawa and Uyeta.

Example 7

4-Methylstyrene

TLC R$_f$=0.70 (pentane); IR (CCl$_4$) 3089 (m), 3048 (m), 3009 (s), 2962 (s), 2962 (s), 2926 (s), 2855 (s), 1628 (m), 1570 (s), 1513 (s); $^1$H NMR (200 MHz, CDCl$_3$) δ2.32 (s, 3H), 2.59 (d, J=10.9, 1H), 2.56 (d, J=17.6, 1H), 6.67 (dd, J=17.5, 10.9, 1H), 7.12 (d, J=8.0, 2H), 7.29 (d, J=8.1, 2H); $^{13}$C NMR (CDCl$_3$) δ21.2, 112.8, 126.1, 129.2, 134.8, 136.7, 137.6; LRMS (EI) 119((M+1), 11), 118 ((M$^+$), 100), 117 (68), 91 (42); HRMS (EI) calculated for C$_9$H$_{10}$ 118.0783 (M$^+$), found 118.0777. The IR and $^1$H NMR matched spectral data reported by Hollywood, F. and Suschitzaky, H., *Synthesis* 662–665 (1982).

Example 8

4-Allytoluene

TLC R$_f$=0.55 (pentane); IR (CCl$_4$) 3126 (w), 3082 (m), 3049 (s), 3005 (s), 2980 (s), 2923 (s), 2853 (m), 1639 (s), 1576 (s), 1514 (s); $^1$H NMR (200 MHz, CDCl$_3$) δ8 2.31 (s, 3H), 3.34 (d, J=6.7, 2H), 5.01 (t, J=1.4, 1H), 5.06–5.10 (m, 1H), 5.88–6.02 (m, 1H), 7.04–7.20 (m, 4H); $^{13}$C NMR (CDCl$_3$) δ8 21.0, 39.8, 115.5, 126.8, 128.4, 129.1, 135.5, 137.8; LRMS (EI) 132 ((M$^+$), 12), 131 (13), 117 (81), 91 (100); HRMS (EI) calculated for C$_{10}$H$_{12}$ 132.0939 (M$^+$), found 132.0940. The $^1$H NMR matched spectral data reported by Fueno, T. et al., *Bull. Chem. Soc. Jpn.* 46:1418–1421 (1973).

Example 9

Preparation of Allylic Alcohol Derivatives

3-Benzoyl-cyclohexene

To a solution of 0.320 g (3.26 mmol) of 2-cyclohexen-1-ol and 0.76 mL (9.40 mmol) of pyridine in 20 mL of CH$_2$Cl$_2$ was added 1.04 mnL (8.96 mmol) of benzoyl chloride via syringe. The reaction mixture was yellow with a white precipitate. The reaction was stirred at room temperature for 17 h. The reaction was quenched by the addition of 50 mL of H$_2$O; the aqueous layer was washed with 4×50 mL of Et$_2$O, and the combined organic layers were dried over MgSO$_4$ and concentrated in vacuo. Purification of the residue by flash chromatography (35 mm, 20 cm, 10% CH$_2$Cl$_2$/hexane) gave 0.635 g (99%) of 3-benzoylcyclohexene as a pale yellow oil: TLC R$_f$=0.35 (10% CH$_2$Cl$_2$/hexane); IR (CCl$_4$) 3100 (w), 3081 (w), 3038 (w), 2931 (s), 1725 (s), 1550 (s); $^1$H NMR (CDCl$_3$) δ1.66–2.12 (m, 6H), 5.49 (bs, 1H), 5.79–5.83 (m, 1H), 5.97–6.01 (m, 1H), 7.41 (t, J=7.7, 2H), 7.52 (t, J=7.4, 1H); 8.02–8.04 (m, 2H); $^{13}$C NMR (CDCl$_3$) δ19.0, 25.0, 28.4, 68.6, 125.8, 128.3, 129.6, 130.9, 132.7, 132.8, 166.2; LRMS (EI) 203 ((M+1), 3), 202 ((M$^+$), 20), 105 (100); HRMS (EI) calculated for C$_{13}$H$_{14}$O$_2$ 202.0994 (M$^+$), found 202.1003. The IR, $^1$H NMR, and $^{13}$C NMR matched spectral data reported by Akemark, B. et al., *J. Org. Chem.* 59:5729–5799 (1994).

Example 10

(+)-(R,R)-cis-Carveolbenzoate

To a solution of (R)-(−)-carvone and 19.269 g (951.72 mmol) of CeCl$_3$-7H$_2$O in 97 mL of anhydrous MeOH was added 2.026 g (53.56 mmol) of NaBH$_4$ via a solid addition funnel. The NaBH$_4$ was slowly added over a period of 10 min. The reaction was stirred at room temperature for 1.5 h. The reaction was quenched by the addition of 200 mL of H$_2$O; the aqueous layer was washed with 4×250 mL of Et$_2$O, and the combined organics were washed with 3×200 mL of saturated NaCl and 1×200 mL of H$_2$O. The reaction was dried over MgSO$_4$ and concentrated in vacuo. The crude product was >95% pure by GC and indicated a 32.9:1 ratio of cis/trans alcohols was present. The yield was 6.16 g (87%) of a clear oil. The $^1$H NMR (200 MHz) matched spectral reported by Nonoshita, K. et al., *Bull. Chem. Soc.* 61:2241–2243 (1988), so further characterization was not performed. IR and elemental analysis results may be found in Nonoshita, K. et al.

To a solution of 1.859 g (12.21 mmol) of carveol and 3.98 mL (32.26 mmol) of pyridine in 145 mL of CH$_2$Cl$_2$ was added 4.60 mL (37.00 mmol) of benzoyl chloride via syringe. The yellow reaction was stirred at room temperature for 24 h. The reaction was quenched by the addition of 200 mL of H$_2$O; the aqueous layer was washed with 1×100 mL of each of the following: 10% HCl, 10% NaHCO$_3$, saturated NaCl, and H$_2$O, and the extracts were dried with MgSO$_4$ and concentrated in vacuo. Purification of a 1.004 g portion of the crude material by flash chromatography (50 mm, 17 cm, 10% EtOAc/hexane) gave 0.441 g (44%) of pure (+)-(R,R)-cis-carveolbenzoate: TLC R$_f$=0.43; [α]$^{27}$$_D$=+17.0 (c=3.70, EtOH)(lit. Utagawa, A. et al., *Bull. Chem. Soc. Jpn.* 61:1207–1212 (1988) [α]$^{22}$$_D$=13.3 (c=1.25, EtOH). The IR and $^1$H NMR were identical to spectral data reported by Utagawa et al., so further characterized was not performed.

Example 11

Cross-Coupling Reactions Utilizing Allylic Alcohol Derivatives

3-Phenylcyclohexene

TLC R$_f$=0.67 (10% CH$_2$Cl$_2$/hexane); IR (CCl$_4$) 3088 (m),3063 (m),3025 (s), 2938 (s), 2863 (s), 2838 (s), 1656 (w), 1606 (m), 1543 (m); $^1$H NMR (CDCl$_3$) δ0.85–2.09 (m, 6H), 3.38 (bs, 1H), 5.70 (dd, J=10.0, 2.1, 1H), 5.86–5.88 (m, 1H), 7.16–7.30 (m, 5H); $^{13}$C NMR (CDCl$_3$) δ21.2, 22.7, 32.6, 41.8, 125.9, 127.7, 128.2, 128.3, 130.2, 146.6; LRMS (EI) 159 ((M+1), 15), 158 ((M$^+$), 100), 143 (43), 129 (79); HRMS (EI) calculated for C$_{12}$H$_{14}$ 158.1096 (M$^+$), found 158.1098. The IR, $^1$H NMR and $^{13}$C NMR, and MS matched spectral data reported by Arnold, D. R. and Mines, S. A., *Can. J. Chem.* 67:689–698 (1989).

Example 12

(R,S)-trans-2-Methyl-3-phenyl-5-isopropenyl-1-cyclohexene

TLC R$_f$=0.43 (10% CH$_2$Cl$_2$/hexane). The $^1$H NMR spectrum (200 MHz) matched spectral data from compounds made previously. See Brescia, M. -R and DeShong, P., *J. Org. Chem.* 63:3156–3157 (1998).

Example 13

General Procedure for the Cross Coupling Reactions Utilizing Aryl Iodides, Bromides, and Chlorides 4-Acetylbiphenyl To a solution of 0.101 g (0.410 mmol) of 4'-iodoacetophenone and 1.113 g (2.062 mmol) of TBAT in 10 mL of DMF was added 12 mg (0.033 mmol) of allyl palladium chloride dimer. The reaction mixture was degassed to remove oxygen via one freeze-pump-thaw cycle. The red-brown mixture was heated at 95° C. for 5 h. The resulting brown mixture was quenched by the addition of 50 mnL of H$_2$O; the aqueous layer was then extracted with 4×50 mL of Et$_2$O, and the combined organic layers were dried over MgSO$_4$ and concentrated in vacuo. Purification of the residue by flash chromatography (25 mm, 17 cm, 0–10% EtOAc/hexane) gave 70 mg (86%) of 4-acetylbiphenyl as a yellow solid and 7 mg 14%) of 4,4'-diacetylbiphenyl, the homocoupled product. Recrystallization from absolute EtOH yielded pale yellow needles: TLC R$_f$=0.29 (10% EtOAc/hexane); mp 119–119.5° C. (lit. mp 119–120° C. (EtOH) Echavarren, A. M. and Stille, J. K., *J. Am. Chem. Soc.* 109:5478–5486 (1987)); IR (CCl$_4$) 3081 (w), 3038 (w), 3000 (w), 2931 (m), 2850 (w), 1691 (m), 1569 (s), 1538 (s); $^1$H NMR δ2.63 (s, 3H), 7.88 (t, J=7.3, 1H), 7.46 (t, J=7.4, 2H), 7.61 (d, J=7.2, 2H), 7.67 (A of AB quartet, J$_{AB}$=8.4, 2H), 8.02 (B of AB quartet, J$_{AB}$=8.4, 2H); $^{13}$C NMR δ26.6, 127.2, 128.2, 128.9, 135.9, 139.9, 145.8, 197.7; LRMS (EI) 197 ((M+1), 10), 196 ((M$^+$), 59), 181 (100), 158 (35), 152 (41); HRMS (EI) calcd for C$_{14}$H$_{12}$O 196.0888 (M$^+$); found 196.0883. The IR and $^1$H NMR are identical to the spectral reported by Echavarren and Stille.

Example 14

3-Methylbiphenyl

TLC R$_f$=0.47 (10% Et$_2$O/pentane); IR (CCl$_4$) 3093 (w), 3069 (s), 3031 (s), 2969 (m), 2931 (s), 2869 (w), 1600 (s), 1575 (s), 1531 (m); $^1$HNMR (CDCl$_3$) δ2.28 (s, 3H), 7.23–7.28 (m, 4H), 7.32–7.35 (m, 3H), 7.39–7.43 (m, 2H); $^{13}$C NMR (CDCl$_3$) δ20.8, 126.1, 127.1, 127.6, 128.4, 129.1, 129.5, 130.1, 130.6; LRMS 169 ((M+1), 17), 168 ((M$^+$), 100), 167 (54), 165 (23), 152 (21); HRMS (EI) calcd for C$_{12}$H$_{12}$ 168.0939 (M$^+$); found 168.0941. The IR and $^1$H NMR are identical to the spectral data reported by Rao, M. S. C. and Rao, G. S. K.

Example 15

2-Methylbiphenyl

TLC R$_f$=0.59 (10% Et$_2$O/pentane); IR (CCl$_4$) 3063 (m), 3025 (m), 2963 (w), 2925 (m), 2869 (w), 1600 (s), 1550 (s);

¹H NMR (CDCl₃) δ2.27 (s, 3H), 7.22–7.44 (m, 9H); ¹³C NMR (CDCl₃) δ21.9, 124.6, 127.5, 128.8, 129.0, 138.7, 141.6; LRMS 169 ((M+1), 20), 168 ((M⁺), 100), 167 (85), 165 (41), 153 (34), 152 (28); HRMS (EI) calcd for C₁₃H₁₂ 168.0939 (M⁺); found 168.0937. The IR, ¹H NMR and HRMS are identical to the spectral data reported by Rieke, R. D. et al., *J. Am. Chem. Soc.* 112:8388–8398 (1990).

The Triflates were prepared using a modification of a procedure reported by Ritter, K., *Synthesis* 735–762 (1993) as follows.

Example 16

4-Tolyl Trifluoromethanesulfonate

To a 0° C. solution of 1.002 g (9.27 mmol) of p-cresol in 5.3 mL of pyridine was added 2.37 mL (14.09 mmol) of triflic anhydride. The reaction turned brownish-yellow upon addition of the triflic anhydride. The reaction was stirred at room temperature for 1.75 h. The resulting mixture was quenched by this addition of 30 mL of H₂O; the aqueous layer was then extracted with 2×30 mL of Et₂O, and the combined organic layers were washed with 30 mL of 10% HCl and 30 mL of saturated NaCl and then dried over MgSO₄ and concentrated in vacuo. This yielded 2.131 g (96%) of a yellow oil that was 96% pure by GC. Purification of the residue by column chromatography (15 mm, 19 cm, 25% Et₂O/pentane) gave 1.956 g (88%) of a colorless oil: TLC R$_f$=0.75 (25% Et₂O/pentane); IR (CCl₄) 3050 (w), 2988 (w), 2938 (w), 2869 (w), 1600 (m), 1556 (m), 1506 (s); ¹H NMR (CDCl₃) δ2.36 (s, 3H), 7.14 (A of AB quartet, J$_{AB}$=8.6, 2H), 7.22 (B of AB quartet, J$_{AB}$=8.6, 2H); ¹³C NMR (CDCl₃) δ20.7, 118.8 (q, J$_{C-F}$=320), 121.0, 130.7, 138.5, 147.6; LRMS 241 ((M+1), 4), 240 ((M⁺), 48), 107 (100), 77 (46); HRMS (EI) calcd for C₈H₇O₃F₃S (M⁺) 240.0068, found 240.0061. The IR and ¹H NMR and HRMS are identical to the spectral data reported by Cabri, N. et al., *J. Org. Chem.* 57:1481–1486 (1992) and the LRMS is identical to data found in Derocque, J. -L., and Jochem, M., *Org. Mass. Spectrom.* 12:479–487 (1977). Elemental analysis data can be found in Cabri, N. et al.

Example 17

Phenyl Trifluoromethanesulfonate

TLC R$_f$=0.53 (25% EtOAc/hexane); IR (CCl₄) 3066 (w), 1602,1488 (m), 1427 (s), 1248 (m), 1225 (m), 1206 (m), 1173 (m), 1145 (s); ¹H NMR (CDCl₃) δ7.25–7.27 (m, 2H), 7.38–7.40 (m, 1H), 7.43–7.45 (m, 2H). The IR and ¹H NMR and HRMS are identical to the spectral data reported by Anders E. and Stankowiak, M., *Synthesis* 1039–1041 (1984). Additional spectral information (¹³C, ¹⁹F, and GC/MS data) can be found in Olah, G. A. and Wu, A., *Synthesis* 204–206 (1991).

Example 18

4-Nitrophenyl Trifluoromethansulfonate

TLC R$_f$=0.37 (25% Et₂O/hexane); mp 50.5–52° C. (lit. mp 53–54° C.); Stille, J. K. etal., *Org. Synth.* 71:97–106 (1993); IR (CCl₄) 3119 (w), 3087 (w), 3006 (w), 1717 (s), 1620 (m), 1488 (m), 1436 (s), 1348 (s); ¹H NMR (CDCl₃) δ7.45–7.48 (m, 2H), 8.34–8.37 (m, 2H); ¹³C NMR (CDCl₃) 118.6 (q, J$_{C-F}$=321), 122.5, 126.0, 147.2, 153.1. The IR and ¹H NMR are identical to the spectral data reported by Stille, J. K. et al., *Org. Synth.* 71:97–106 (1993). Stille et al. also reports the HRMS data. IR and ¹H NMR data is reported by Echavarren, A. M. and Stille, J. K., *J. Am. Chem Soc.* 109:5478–5486 (1987). LRMS data can be found in Derocque, J. -L. and Jochem, M., *Org. Mass Spectrom.* 12:479–487 (1977).

Example 19

4-Acetylphenyl Trifluoromethanesulfonate

TLC R$_f$=0.38 (25% Et₂O/hexane); IR (CCl₄) 3107 (w), 3070 (w), 3009 (w), 1649 (s), 1600 (m); ¹H NMR (CDCl₃) δ2.61 (s, 3H), 7.36 (A of AB quartet, J$_{AB}$=8.8, 2H), 8.04 (B of AB quartet, J$_{AB}$=8.8, 2H); ¹³C NMR (CDCl₃) δ26.8, 118.6(q, J$_{C-F}$=321),121.4, 130.4, 136.8, 152.3, 195.9. The IR and ¹H NMR are identical to the spectral data reported by Echavarren and Stille. Elemental analysis results are available in Echavarren and Stille.

Example 20

4-Carbomethoxyphenyl Trifluoromethanesulfonate

TLC R$_f$=0.35 (10% EtOAc/hexane); IR (CCl₄) 3000 (w), 2954 (m), 2845 (w), 1924 (w), 1732 (s), 1604 (m), 1499 (m), 1430 (s), 1412 (s), 1284 (s); ¹H NMR (CDCl₃) δ3.92 (s, 3H), 7.33 (m, 2H), 8.18 (m, 2H); ¹³C NMR (CDCl₃) δ52.4, 118.7 (q, J$_{C-F}$=320),121.4, 130.4, 131.8, 152.5, 165.4; LRMS 285 ((M+1), 8), 284 ((M⁺), 76), 253 (100), 189 (89), 123 (28), 95 (33), 70 (32); HRMS (EI) calcd for C₉H₇O₅F₃S (M⁺) 283.9966, found 283.9965. The ¹H NMR is identical to the spectral data reported by Percec, V. et al., *J. Org. Chem.* 60:176–185 (1995).

Example 21

1-Naphthyl Trifluoromethanesulfonate

TLC R$_f$=0.51 (10% EtOAc/hexane); IR (CCl₄) 3062 (m), 1602 (m), 1508 (m), 1418 (s), 1388 (s), 1231 (m), 1201 (m), 1145 (s), 1071 (m), 1030 (m), 901 (s); ¹H NMR (CDCl₃) δ7.44–7.50 (m, 2H), 7.57–7.65 (m, 2H), 7.85–7.92 (m, 2H), 8.07 (d, J=8.2, 1H). The IR and ¹H NMR are identical to the spectral data reported by Echavarren and Stille. ¹³C NMR, LRMS, and elemental analysis results can also be found in Crisp, G. T. and Papadopoulos, S., *Aust. J. Chem.* 41:1711–1715 (1988).

Example 22

Cross Coupling Reactions: 4-Nitrobiphenyl

TLC R$_f$=0.56; mp 111.5–112° C. (lit. mp 113–115° C. (MeOH); Wallow, T. I. and Novak, B. M., *J. Org. Chem.* 59:5034–5037 (1994)); IR(CCl₄) 3067 (w), 3034 (w), 1604 (m), 1521 (w), 1347 (s); ¹H NMR (CDCl₃) δ7.47–7.49 (m, 3H), 7.61 (d, J=7.2, 2H), 7.72 (A of AB quartet, J$_{AB}$=8.7, 2H), 8.29 (B of AB quartet, J$_{AB}$=8.7, 2H). The ¹H NMR is identical to spectral data reported by Wallow, T. I. and Novak, B. M. Additional spectral information (13C NMR and MS data) can be found in Wallow, T. I. and Novak, B. M.

Example 23

4-Carbomethoxybiphenyl

TLC R$_f$=0.37; mp108–108.5° C. (lit. mp 116–117 (hexane/EtOAc), Barba, I., et al., *Tetrahedron* 46:7813–7822 (1990)); IR (CCl₄) 3033 (w), 2952 (w), 1728 (m), 1560 (s), 1279 (s); ¹HNMR (CDCl₃) δ3.92 (s, 3H), 7.30–7.40 (m, 1H), 7.40–7.50 (m, 2H), 7.60–7.66 (m, 4H), 8.09 (d, J=8.3, 2H). The IR and $^1$H NMR are identical to spectral data reported by Barba, I., et al.

Example 24

1-Phenylnaphthylene

TLC $R_f$=0.54; mp191–199° C.; IR (CCl$_4$) 3071 (w), 3058 (w), 2986 (w), 1569 (s), 1533 (s), 1252 (s), 1533 (s), 1252 (s), 1217 (s), 1118 (s), 1006 (s), 834 (s); $^1$H NMR (CDCl$_3$) δ7.21–7.25 (m, 2H), 7.33–7.35 (m, 4H), 7.43–7.46 (m, 6H), GC/MS 205 ((M+1), 13), 204 ((M$^+$), 92), 203, (100), 202 (56), 101 (66). The IR and LRMS data are identical to spectral data reported by Hoffman, J., et al., *Liebigs Ann Chem.* 631–636 (1995)

Example 25 N-Phenethyl-2-phenylacetamide

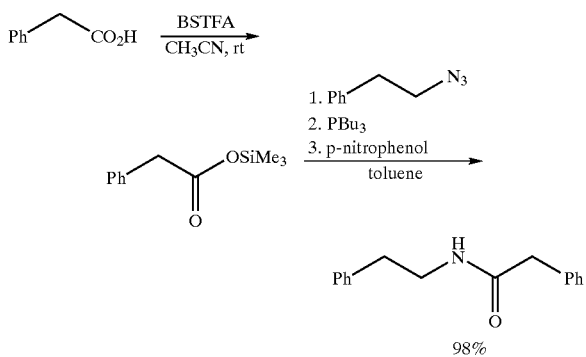

98%

To an argon-blanketed solution of phenylacetic acid (69 mg, 0.51 mmol) in acetonitrile (3 mL) was added bis(trimethylsilyltrifluoroacetamide) (BSTFA, 400 μL, 1.51 mmol) via syringe. The mixture was stirred for 30 min. after which time solvent, unreacted starting material and the reaction by-products were removed at high vacuum. The colorless residue was redissolved in toluene (5 mL) and phenethyl azide (58 mg, 0.39 mmol) then freshly-distilled tri-n-butylphosphine (98 μL, 0.39 mmol) were added via syringe. While nitrogen evolution was still progressing, p-nitrophenol (55 mg, 0.40 mmol) was added in one portion, imparting a bright yellow color to the solution. The reaction was stirred at 65° C. for 48 h. The reaction mixture was partitioned between satd Na$_2$CO$_3$ solution and ethyl acetate. The organic layer was dried over sodium sulfate, filtered and concentrated in vacuo to give a yellow oil that was purified by flash chromatography (1:1 EtOAc/hexane) to yield 91 mg (98%) of the title compound as a white powder (mp 91–92° C., lit. mp 91–93° C.). Spectral data were identical to those reported in the literature.

Example 26

1,2,3,4-Tetra-O-acetyl-6-azido-6-deoxy-β-D-glucopyranose

Trimethylsilyl azide (40 μL, 0.300 mmol) and TBAF (300 μL, 0.310 mmol) were added to an argon-blanketed solution of tosylate 42a (109 mg, 0.217 mmol) in 4 mL of CH$_3$CN. The reaction was heated at reflux for 6 h. Over this time, the solution turned from colorless to clear yellow. The mixture was allowed to return to room temperature, and 10 mL of water was added. This material was extracted with ethyl acetate. The organic extracts were combined, dried over Na$_2$SO$_4$, and filtered. Solvent was removed in vacuo to afford a light yellow oil. This oil was purified by flash chromatography (2:1, EtOAc/hexane) to yield 62 mg (77%) of azide as a colorless oil. IR (CCl$_4$) 2106, 1756; $^1$H NMR (CDCl$_3$) δ5.84 (d, J=1.2 Hz, 1H), 5.46 (dd, J=3.1, 1.2, 1H), 5.24 (dd, J=9.6, 9.6 1H), 5.09 (dd, J=9.6, 3.1, 1H), 3.74 (ddd, J=9.6, 5.5, 3.5, 1H), 3.42–3.34 (m, 2H), 2.20 (s, 3H), 2.09 (s, 3H), 2.04 (s, 3H), 1.99 (s, 3H), $^{13}$C NMR (DCDl$_3$) δ170.2, 169.8, 169.7, 168.4, 90.1, 74.4, 70.5, 68.0, 66.4, 50.7, 20.8, 20.7, 20.6, 20.5.

Example 27

1,3,4,6-Tetra-O-acetyl-2-azido-2-deoxy-β-D-glucopyranose 1,3,4,6-Tetra-O-acetyl-2-O-trifluormethanesulfonyl-β-D-mannopyranose (6) (53 mg, 0.11 mmol) was dissolved at 25° C. in 3 mL of THF. Trimethylsilyl azide (19 μL, 0.15 mmol) was added via syringe followed by TBAF (150 μL, 0.15 mmol). The solution was stirred at 25° C. for 22 h. The reaction mixture was filtered through a plug of silica gel and concentrated in vacuo to give a yellow oil which was chromatographed (2:1, hexane/EtOAc) to afford 30 mg (73%) of β-anomer as a colorless oil. IR (CCl$_4$) 2113, 1762; $^1$H NMR (CDCl$_3$) 5.56 (d, J=8.8), 5.10 (t, J=9.5), 5.05 (t, J=9.5), 4.31 (dd, J=4.8, 12.5), 4.09 (dd, J=12.5), 3.79 (ddd, J=9.5, 4.8, 2.0), 3.65 (dd, J=9.5, 8.8), 2.18 (s, 3H), 2.08 (s, 3H), 2.06 (s, 3H), 2.01 (s, 3H). The spectra for the anomeric mixture has been previously reported (Vasella, A. et al., *Helv. Chim. Acta* 74:2073–2077 (1991)).

Example 28

2,3,4,6-Tetra-O-acetyl-β-D-glucopyranosyl Azide

Method a (Entry c, Table 3). 2,3,4,6-Tetra-O-acetyl-α-D-glucopyranosyl bromide (42c) (89 mg, 0.22 mmol) was dissolved at 25° C. in 3 mL of THF. Trimethylsilyl azide (40 μL, 0.3 mmol) was added via syringe followed by TBAF (0.3 mL, 0.3 mmol). The solution was stirred at 25° C. for 3 h. The organic solution was filtered through a plug of silica gel, dried over Na$_2$SO$_4$, and concentrated in vacuo to give a yellow amorphous solid. The residue was crystallized from absolute ethanol to afford 75 mg (93%) of azide 43cβ as a white solid: mp 126–127° C. mp 126–128° C.; Ogawa, T., et al., *Agric. Biol. Chem.* 47:281–285 (1983)). Physical and spectroscopic properties of 43cβ were identical to previously reported data (Ogawa, T., et al., *Agric. Biol. Chem.* 47:281–285 (1983); Sabesan, S. and Neira S., *Carbohydr. Res.* 223:169–185 (1992)).

Method b (Entry d, Table 3). 2,3,4,6-Tetra-O-acetyl-α-D-glucopyranosyl chloride 42d (Lemioux, R. U., in *Methods in Carbohydrate Chemistry*, Whistler, R. L. et al., (eds.), Academic Press, New York, 2:223–224 (1963)) (10) (80 mg, 0.22 mmol) was dissolved at 25° C. in 3 mL of THF. Trimethylsilyl azide (40 μL, 0.3 mmol) was added via syringe followed by TBAF (0.3 mL, 0.3 mmol). The solution was stirred for 29 h at 65° C. The reaction was cooled to ambient temperature, filtered through a plug of silica gel, dried over Na$_2$SO$_4$, and concentrated in vacuo to give a yellow oil. The oil was crystallized from absolute ethanol to afford 69 mg (85%) of azide 43dβ as a white solid: mp 126–126.5° C.; lit. mp 126–128° C.; Ogawa, T. et al., *Argic. Biol. Chem.* 47:281–285 (1983)). Physical and spectroscopic properties of 43dβ were in agreement with previously reported values (Ogawa, T. et al., *Agric. Biol. Chem.* 47:281–285 (1983); Sabesan, S. and Neira S., *Carbohydr. Res.* 223:169–185 (1992)).

Method c (Entry f, Table 3). 2,3,4,6-Tetra-O-acetyl-α-D-glucopyranosyl trichloroimidate 43f (Schmidt, R. and Stumpp, R., *Liebigs Ann. Chem.* 1249–1256 (1983)) (12) (240 mg, 0.49 mmol) was dissolved at 25° C. in 4 mL of TBIF. Trimethylsilyl azide (90 μL, 0.68 mmol) was added via syringe followed ty TBAF (0.68 mL, 0.68 mmol). The solution was stirred for 22 h at 65° C. The reaction was cooled to ambient temperature, filtered through a plug of silica gel, dried over $Na_2SO_4$, and concentrated in vacuo to give a yellow oil. The oil was crystallized from acetone and recrystallized from $Et_2O$/petroleum ether (1:1) to afford 150 mg (88%) of hydrolyzed sugar 43f as a white solid with no traces of the sugar azide: mp 130–132° C. (lit. mp 132–134° C.; McCloskey, C. M. et al., *J. Am. Chem. Soc.* 66:349–350 (1944)); IR ($CCl_4$) 3462, 1759; $^1H$ NMR ($CDCl_3$) 5.27 (t, J=9.7), 5.09 (t, J=9.7), 4.89 (dd, J=9.7, 8.2), 4.75 (dd, J=8.7, 8.2), 4.26 (dd, J=12.3,4.7), 4.15 (dd, J=12.3, 2.3), 4.75 (ddd, J=9.7, 4.7, 2.4), 3.62 (d, J=8.7), 2.07 (s, 3H), 2.06 (s, 3H), 2.00 (s, 3H), 1.99 (s, 3H).

Example 29

2,3,4,6-Tetra-O-acetyl-D-glucopyranosyl Azide 2,3,4,6-Tetra-O-acetyl-β-D-glucopyranosyl chloride (42e) (Lemieux, R. U., in *Methods in Carbohydrate Chemistry*, Whistler, R. L. et al., (eds.), Academic Press, New York, 2:224–225 (1963)) (11) (80 mg, 0.22 mmol) was dissolved at 25° C. in 3 mL of THF. Trimethylsilyl azide (40 μL, 0.3 mmol) was added via syringe followed by TBAF (0.3 mL, 0.3 mmol). The solution was stirred for 46 h at 65° C. The reaction was cooled to ambient temperature, filtered through a plug of silica gel, dried over $Na_2SO_4$, and concentrated in vacuo to give a yellow amorphous material which was crystallized from absolute ethanol. The crude reaction mixture was 9:1 (α/β) anomeric mixture of 2,3,4,6-tetra-O-acetyl-D-glucopyranosyl azide (43e) as determined by $^1H$ NMR. The anomeric mixture was separated by column chromatography (4:1, hexane/EtOAc) and crystallized from absolute ethanol to effort 8 mg (10%) of azide 43eβ as a white solid and 69 mg (90%) of azide 43eα as a white solid (overall yield of 95%) with melting point of 98–99° C. (lit. mp 98–99.5° C. Physical and spectroscopic properties of azide 43eα were identical to previously reported values (Ogawa, T. et al., *Agric. Biol. Chem.* 47:281–285 (1983); Sabesan, S. and Neira S., *Carbohydr. Res.* 223:169–185 (1992)).

Example 30

2,3,4,6-Teira-O-benzyl-β-D-glucopyranosylAzide

Method a (Entry g, Table 3). 2,3,4,6-Tetra-O-benzyl-α-D-glucopyranosyl chloride (42g) (Grynkiewicz, G. and J. N. BeMillor, *Carbohydr. Res.* 131:273–276 (1984)) (14) (100 mg, 0.18 mmol) was dissolved at 25° C. in 3 mL of THF. Trimethylsilyl azide (32 μL, 0.25 mmol) was added via syringe followed by TBAF (0.25 mL, 0.25 mmol). The solution was stirred for 5 h at 65° C. The reaction was cooled to ambient temperature, filtered through a plug of silica gel, dried over $Na_2SO_4$, and concentrated in vacuo to give a yellow oil. The oil was chromatographed (9:1, hexane/EtOAc) to afford 94 mg (92%) of azide 43gβ as a colorless oil. Physical and spectroscopic properties of azide 43gβ were identical to previously reported values (Ogawa, T. et al., *Agric. Biol. Chem.* 47:281–285 (1983)).

Method b (Entry h, Table 3). 2,3,4,6-Tetra-O-benzyl-α-D-glucopyranosyl trichloroimidate (Schmidt, R. R. and J. Michel, *Angew. Chem. Int. Ed. Engl.* 19:731–732 (1980)) (16) (790 mg, 1.15 mmol) was dissolved at 25° C. in 30 mL of THF. Trimethylsilyl azide (0.21 mL, 1.58 mmol) was added via syringe followed by TBAF (1.58 mL, 1.58 mmol). The solution was stirred for 48 h at 65° C. The reaction was cooled to ambient temperature, filtered through a plug of silica gel, dried over $Na_2SO_4$, and concentrated in vacuo to give a yellow oil. The oil was chromatographed (9:1 hexane/EtOAc) to give 310 mg (48%) of an inseparable anomeric mixture (1:1, α/β) of azide 43e as a colorless oil. Spectroscopic and physical properties of the anomeric mixture were in agreement with previously reported values (Ogawa, T. et al., *Agric. Biol. Chem.* 47:281–285 (1983)).

Example 31

2-Acetamido-3,4,6-tri-O-acetyl-2-dexoy-β-D-glucopyranosyl Azide

Method a (Entry i, Table 3). 2-Methyl-(3,4,6-tri-O-acetyl-1,2-dideoxy-α-D-glucopyrano)-[2,1-d]-2-oxazoline (42i) (Nakabayashi, S., etal., *Carbohyd. Res.* 150:C7–C10(1986); Jha, R. and J. T. Davis, *Carboydr. Res.* 277:125–134 (1995)) (17) (110 mg, 0.33 mmol) was dissolved at 25° C. in 3 mL of THF. Trimethylsilyl azide (60 μL, 0.44 mmol) was added via syringe followed by TBAF (0.44 mL, 0.44 mmol). The solution was stirred for 22 h at 65° C. The reaction was cooled to ambient temperature, filtered through a plug of silica gel, dried over $Na_2SO_4$, and concentrated in vacuo to give a yellow oil. The oil was crystallized from EtOAc/petroleum ether to afford 89 mg (73%) of azide 43i, as a white solid. Physical and spectroscopic properties of 43i were identical to previously reported data (Sabesan, S. and Neira S., *Carbohydr. Res.* 223:169–185 (1992)).

Method b (Entry j, Table 3). 2-Acetamido-3,4,6-tri-O-acetyl-2-deoxy-α-D-glucopyranosyl chloride (42j) (Heidlas, J. E. et al., *J. Org. Chem.* 57:146–151 (1992)) (79 mg, 0.22 mmol) was dissolved at 25° C. in 8 mL of THF. Trimethylsilyl azide (58 μL, 0.43 mmol) was added via syringe followed by TBAF (0.43 mL, 0.43 mmol). The solution was stirred for 1.5 h at 65° C. The reaction was cooled to ambient temperature, filtered through a plug of silica gel, dried over $Na_2SO_4$ and concentrated in vacuo to give a yellow-brown oil. The oil was chromatrographed (10:1, $CH_2Cl_2$/MeOH) to afford a white solid which was recrystallized from EtOAc/petroleum ether to afford 72 mg (89%) of azide 43j as a white solid. Physical and spectroscopic properties of 43j were identical to previously reported data (Sabesan, S. and Neira S., *Carbohydr. Res.* 223:169–185 (1992)).

Scheme 25

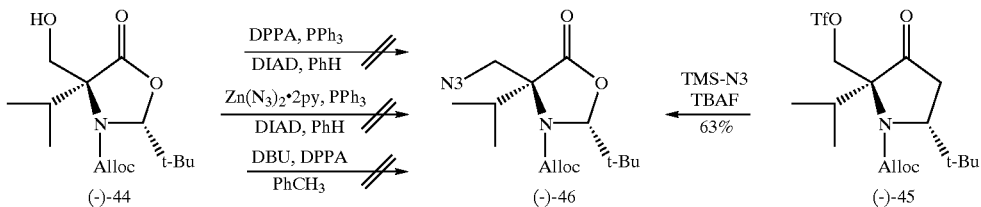

Example 32

Oxazolidinone Azide (−)

Carbinol (−)-44 (Alcohol (−)-44 was prepared according to the method of Favor: Favor, D. A. Ph.D., Thesis, University of Pennsylvania, 1999) (1.01 mL, 3.36 mmol) and 2,6-di-tert-butyl-4-methylpyridine (1.17 g, 5.71 mmol) were dissolved in 34 mL of $CH_2Cl_2$. Trifluoromethane sulfonic anhydride (0.79 mL, 4.70 mmol) was added at 0° C. After 1 h at 0° C., the reaction was quenched with saturated aqueous $NaHCO_3$ (20 mL), washed with $CH_2Cl_2$, dried over $MgSO_4$, and concentrated in vacuo. The residue was chromatographed (4:1, hexane/EtOAc) to gave 1.23 g (85%) of triflate (−)-45 as a clear coloress oil. This was used immediately in the following step. Triflate (−)-45 (1.23 g, 2.85 mmol) was dissolved in dry $CH_3CN$ (20 mL). Trimethylsilyl azide (508 μL, 4.41 mmol) was added via syringe followed by TBAF (4.13 mL, 4.13 mmol). The solution was stirred at reflux for 12 h. The reaction was cooled to room temperature, water was added (30 mL), the solution was extracted with EtOAc, and the combined organics were washed with brine (50 mnL), dried over $MgSO_4$, and concentrated in vacuo. The residue was chromatographed (4:1, hexane/EtOAc) to afford 590 mg (63%) of azide (−)-46 as a white solid: mp 35–36° C.; $[α]^{20}D$ −9.7° (c 0.59, $CHCl_3$); IR ($CHCl_3$) 3020, 2980, 2110, 1785, 1715; $^1H$ NMR (500 MHz, $CDCl_3$) δ5.93 (ddt, J=17.1, 10.5, 6.2, 1 H), 5.60 (s, 1 H), 5.35 (dd, J=17.1, 1.2, 1 H), 5.28 (d, J=10.4, 1 H), 4.68 (dd, J=12.8,6.0, 1 H), 4.58 (dd, J=12.6, 6.3, 1 H), 2.26 (septet, J=7.0, 1 H), 1.13 (d, J=7.0, 6 H), 0.98 (s, 9 H); $^{13}C$ NMR (125 MHz, $CDCl_3$) δ172.7, 155.0, 131.6, 119.6, 95.6, 68.8, 67.1, 51.2, 37.4, 34.6.25.8, 18.7,17.8; high-resolution mass spectrum (CI, $NH_3$) m/z 325.1879 [(M+H)$^+$; calcd for $C_{15}H_{25}O_4N_4$ 325.1876].

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims. All patents and publications cited herein are incorporated by reference herein in their entirety.

What is claimed is:

1. A transmetallation reaction, comprising:

contacting a palladium catalyst with 1) an aroyl, alkanoyl, or aralkanoyl ester of an allylic alcohol; and 2) a hypervalent silicon species.

2. The reaction of claim 1 wherein the silicon species is tetrabutylammonium triphenyldifluorosilicate.

3. A method for the preparation of a compound having Formula IV:

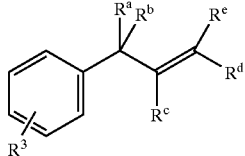

where $R^3$ is zero to three substituents, each of which is independently alkyl, alkenyl, aryl, alkanoyl, alkoxy or nitro and $R^a$, $R^b$, $R^c$, $R^d$ and $R^e$ are independently hydrogen, alkyl, alkenyl, or $R^a$ and $R^e$ together form an optionally substituted carbocyclic or heterocyclic ring, comprising reacting a compound of Formula III:

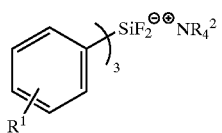

where $R^1$ is zero to three substituents, each of which is independently alkyl, alkenyl, aryl, alkanoyl, alkoxy or nitro, and $R^2$ is an alkyl group with a compound of Formula V:

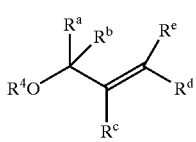

where $R^a$–$R^e$ are defined above and $R^4$ is an aroyl, alkanoyl or aralkanoyl group, wherein the reaction is carried out in the presence of a Pd catalyst, under conditions whereby said compound of Formula IV is produced.

4. The method of claim 3, wherein $R^a$ and $R^e$ together form a five or six membered oxygen containing ring.

5. The method of claim 4, wherein said five or six membered oxygen containing ring is a glycofuranosyl or glycopyranosyl ring with protected hydroxy groups.

6. The method of claim 3, wherein said Pd catalyst is $Pd(dba)_2$.

7. The method of claim 3, wherein the reaction is carried out in THF.

8. A method for the preparation of a compound having Formula IV:

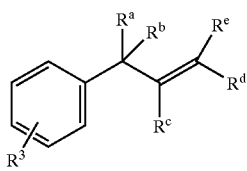

IV where R³ is zero to three substituents, each of which is independently alkyl, alkenyl, aryl, alkanoyl, alkoxy or nitro and $R^a$, $R^b$, $R^c$, $R^d$ and $R^e$ are independently hydrogen, alkyl, alkenyl, or $R^a$ and $R^e$ together form an optionally substituted carbocyclic or heterocyclic ring, comprising reacting a compound of Formula VI:

VI wherein

Y is

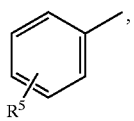,

R⁵ is zero to three substituents, each of which is independently alkyl, alkenyl, aryl, alkanoyl, alkoxy or nitro, and R⁶ is alkyl or fluoroaryl, with a source of fluoride ions or where the compound of Formula VI is added to the reaction as a preformed hypervalent fluoride, and a compound having Formula V:

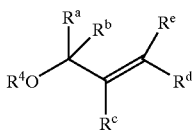

V where $R^a$–$R^e$ are defined above and R⁴ is an aroyl, alkanoyl or aralkanoyl group, wherein the reaction is carried out in the presence of a Pd catalyst, under conditions whereby said compound of Formula IV is produced.

9. The method of claim 8, wherein the compound having Formula IV has the Formula VII:

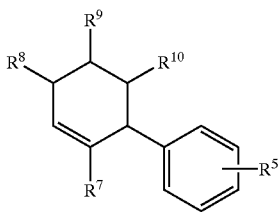

VII wherein R⁷, R⁸, R⁹ and R¹⁰ are independently hydrogen, optionally substituted alkyl or optionally substituted alkenyl.

10. A method for the preparation of a compound having Formula VIII:

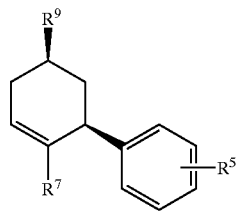

VIII wherein R⁵ is zero to three substituents, each of which is independently alkyl, alkenyl, aryl, alkanoyl, alkoxy or nitro and R⁷ and R⁹ are independently hydrogen, optionally substituted alkyl or optionally substituted alkenyl, by the coupling of a compound having Formula IX:

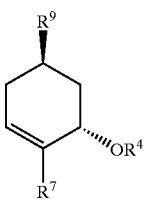

IX wherein R⁴ is an aroyl, alkanoyl or aralkanoyl group, with a compound of Formula VI:

VI wherein

Y is

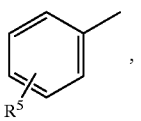, and

R⁶ is alkyl;

in the presence of a source of fluoride ions or where the compound of Formula VI is added as a preformed hypervalent fluoride; and a Pd catalyst, under conditions whereby said compound of Formula IX is produced.

11. The method of claim 10, wherein the source of fluoride ions is a tetraalkylammonium fluoride.

12. A method for the preparation of a compound having Formula X:

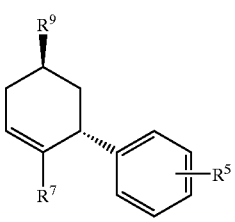

X wherein R⁵ is zero to three substituents, each of which is independently alkyl, alkenyl, aryl, alkanoyl, alkoxy or nitro and $R^7$ and $R^9$ are independently hydrogen, optionally substituted alkyl or optionally substituted alkenyl, by the coupling of a compound having Formula XI:

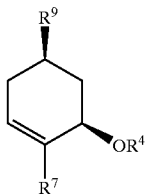
XI wherein $R^4$ is an aroyl, alkanoyl or aralkanoyl group; with a compound of Formula VI:

VI wherein
Y is

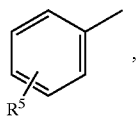

and
$R^6$ is alkyl;
in the presence of a source of fluoride ions or where the compound of Formula VI is added as a preformed hypervalent fluoride; and
a Pd catalyst, under conditions whereby said compound of Formula XI is produced.

13. A method for the preparation of a protected glycosylazide, comprising reacting a protected glycosyl tosylate, halide, triflate or trichloroimidate with an azidotrialkylsilane in the presence of a source of fluoride ion under conditions whereby said protected glycosylazide is produced.

14. The method of claim 13, wherein said source of fluoride ion is a tetraalkylammonium fluoride.

15. The method of claim 14, wherein said tetralkylammonium fluoride is tetrabutylammonium fluoride.

16. The method of claim 13, wherein said source of fluoride ion is present in a catalytic amount.

17. The method of claim 13, wherein said fluoride ion source is tetrabutylammonium triphenyldifluorosilicate.

18. A modified Staudinger reaction comprising coupling of 1) azides and 2) carboxylic acids, comprising:
transforming the acid or acid ester thereof to a silyl ester and coupling the silyl ester with p-nitrophenol in the presence of a phosphine.

19. A method of preparing a compound having Formula XII:

XII where $R^{11}$ is deoxyglycosyl, optionally substituted alkyl, optionally substituted aralkyl, optionally substituted heteroaralkyl or optionally substituted heterocycloalkyl and $R^{12}$ is alkyl or optionally substituted aralkyl, by reaction of a silyl ester of the Formula XIII:

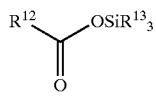
XIII where each $R^{13}$ is independently an alkyl or aryl group, with $R^{11}$—$N_3$ in the presence of a trialkyl or triarylphosphine and a phenol under conditions in which the compound of Formula XII is formed.

20. The method of claim 16, wherein said silyl ester is trimethyl-silylacetate.

21. The method of claim 16, wherein said trialkyl or triarylphosphine is tributylphosphine.

22. The method of claim 16, wherein said phenol is p-nitrophenol.

23. The method of claim 16, wherein said reaction is carried out in toluene.

24. The method of claim 16, wherein said reaction is carried out in dichloroethane.

25. A modified Staudinger reaction comprising coupling a silyl ester of a carboxylic acid with a phosphorimine in the presence of a phenol.

* * * * *